United States Patent
Enomoto et al.

(10) Patent No.: US 10,954,364 B2
(45) Date of Patent: *Mar. 23, 2021

(54) GLOVE DIPPING COMPOSITION, METHOD FOR MANUFACTURING GLOVES, AND GLOVES

(71) Applicant: Midori Anzen Co., Ltd., Tokyo (JP)

(72) Inventors: Norihide Enomoto, Tokyo (JP); Taichi Ogawa, Tokyo (JP)

(73) Assignee: Midori Anzen Co., Ltd., Tokyo (JP)

( * ) Notice: Subject to any disclaimer, the term of this patent is extended or adjusted under 35 U.S.C. 154(b) by 86 days.

This patent is subject to a terminal disclaimer.

(21) Appl. No.: 16/313,500

(22) PCT Filed: Dec. 19, 2017

(86) PCT No.: PCT/JP2017/045570
§ 371 (c)(1),
(2) Date: Dec. 27, 2018

(87) PCT Pub. No.: WO2018/117109
PCT Pub. Date: Jun. 28, 2018

(65) Prior Publication Data
US 2019/0161601 A1 May 30, 2019

(30) Foreign Application Priority Data

Dec. 19, 2016 (JP) .............................. JP2016-246008
Dec. 20, 2016 (JP) .............................. JP2016-247196

(51) Int. Cl.
*C07C 267/00* (2006.01)
*C08L 9/04* (2006.01)
(Continued)

(52) U.S. Cl.
CPC .............. *C08L 15/00* (2013.01); *A41D 19/00* (2013.01); *A41D 19/04* (2013.01); *B29C 41/003* (2013.01);
(Continued)

(58) Field of Classification Search
None
See application file for complete search history.

(56) References Cited

U.S. PATENT DOCUMENTS

2015/0010745 A1* 1/2015 Chieng .................. C08C 19/22
428/220
2018/0371237 A1* 12/2018 Tsukamoto .......... C08G 18/751

FOREIGN PATENT DOCUMENTS

EP 2891668 A1 7/2015
JP 4647026 B2 3/2011
(Continued)

OTHER PUBLICATIONS

International Preliminay Report on Patentability and Written Opinion in International Application No. PCT/JP2017/045570 dated Jul. 4, 2019, 6 pages.

(Continued)

*Primary Examiner* — Richard A Huhn
(74) *Attorney, Agent, or Firm* — Marshall, Gerstein & Borun LLP

(57) ABSTRACT

Provided is: A glove dipping composition including, at least: an elastomer that contains a (meth)acrylonitrile-derived structural unit, an unsaturated carboxylic acid-derived structural unit and a butadiene-derived structural unit in a polymer main chain; a polycarbodiimide; zinc oxide and/or an aluminum complex; water; and at least one pH modifier selected from an ammonium compound and an amine compound, in which glove dipping composition the polycarbodiimide includes at least one polycarbodiimide containing a
(Continued)

hydrophilic segment in its molecular structure and has an average polymerization degree of 3.8 or higher and a carbodiimide equivalent of 260 to 600; the polycarbodiimide is added in an amount of 0.1 to 4.0% by weight and zinc oxide and/or the aluminum complex is/are added in an amount of 0.1 to 5.6% by weight with respect to the total solid content of the glove dipping composition; and the glove dipping composition has a pH of 9.0 to 11.5.

16 Claims, 8 Drawing Sheets

(51) Int. Cl.

| | | |
|---|---|---|
| *C08L 13/02* | (2006.01) | |
| *C08L 33/20* | (2006.01) | |
| *C08F 220/06* | (2006.01) | |
| *C08F 220/46* | (2006.01) | |
| *C08F 236/12* | (2006.01) | |
| *C08C 1/14* | (2006.01) | |
| *C08L 15/00* | (2006.01) | |
| *C08K 5/29* | (2006.01) | |
| *C08F 220/44* | (2006.01) | |
| *C08F 236/06* | (2006.01) | |
| *C08F 265/08* | (2006.01) | |
| *B29C 41/00* | (2006.01) | |
| *B29C 41/14* | (2006.01) | |
| *B29C 41/42* | (2006.01) | |
| *C08K 3/22* | (2006.01) | |
| *A41D 19/04* | (2006.01) | |
| *A41D 19/00* | (2006.01) | |
| *B29K 19/00* | (2006.01) | |
| *B29L 31/48* | (2006.01) | |

(52) U.S. Cl.
CPC ............ *B29C 41/14* (2013.01); *B29C 41/42* (2013.01); *C08F 220/44* (2013.01); *C08F 236/06* (2013.01); *C08F 265/08* (2013.01); *C08K 3/22* (2013.01); *C08K 5/29* (2013.01); *B29K 2019/00* (2013.01); *B29L 2031/4864* (2013.01); *C07C 267/00* (2013.01); *C08C 1/14* (2013.01); *C08F 220/06* (2013.01); *C08F 220/46* (2013.01); *C08F 236/12* (2013.01); *C08K 2003/2296* (2013.01); *C08L 9/04* (2013.01); *C08L 13/02* (2013.01); *C08L 33/20* (2013.01); *C08L 2312/00* (2013.01)

(56) References Cited

FOREIGN PATENT DOCUMENTS

| JP | 2013-203914 A | 10/2013 | |
|---|---|---|---|
| JP | 2015-513486 A | 5/2015 | |
| JP | 5935423 B2 | 6/2016 | |
| KR | 10-1687866 B1 | 12/2016 | |
| WO | WO-2011/068394 A1 | 6/2011 | |
| WO | WO-2013/129905 A1 | 9/2013 | |
| WO | WO-2016/013666 A1 | 1/2016 | |
| WO | WO-2016013666 A1 * | 1/2016 | ........... A41D 19/015 |

OTHER PUBLICATIONS

Search Report in International Application No. PCT/JP2017/045570 dated Feb. 20, 2018, 2 pages.
Extended European Search Report in EP Application No. 17884391.8 dated Oct. 16, 2019, 6 pages.
Database WPI Week 2015487, Thomson Scientific, London, GB; AN 2015-323835, XP002794673 relating to KR 2015 0057092 A, May 28, 2015, 3 pages.
Angus Chemical Company, "Zoldine XL-29SE Crosslinker", Angus Technical Data Sheet, 2016, pp. 1-9, XP002794706, Retrieved from the Internet: URL: https://www.angus.com (retrieved on Oct. 1, 2019), 9 pages.
Office Action in KR Application No. 10-2019-7007489 dated Mar. 10, 2020, 9 pages.

* cited by examiner

| Steps | Operations | Conditions | |
|---|---|---|---|
| (a) Coagulant adhesion step (step of preparing a glove mold to which a coagulant is adhered) | (1) Wash a glove mold. (2) Immerse the glove mold in a liquid coagulant. (3) Dry the glove mold to which the coagulant has adhered. | $Ca(NO_3)_2$ (8 to 40% solution) at 30 to 70°C<br><br>Temperature: preferably 30 to 120°C or 50 to 70°C<br><br>Time: preferably 3 to 30 minutes | |
| (b) Step of aging a dipping composition (step of preparing a dipping liquid in a tank) | (1) Prepare a dipping composition (dipping liquid) by adding a pH modifier and water to an elastomer (XNBR), a CDI, ZnO and/or Al complex, stirring the resultant, and then adjusting the pH to be 9 to 10.5. By controlling the pH in such an alkaline range, -COOH groups are coordinated on the surface side of latex particles, creating a state where reaction is likely to occur.<br>(2) Leave the dipping liquid to stand with continuous stirring (homogenize the dipping liquid by aging). | Room temperature (20°C to 50°C)<br><br><br>Solid content: preferably 10 to 35%<br>Aging time: preferably 5 to 72 hours | |
| (c) Dipping step (step of immersing the glove mold in the dipping liquid and coagulating the XNBR on the glove mold) | (1) Immerse the glove mold, to which the coagulant has adhered, in the dipping liquid.<br>(2) Withdraw the glove mold from the dipping liquid.<br>(3) Depending on the case, the immersion operation is performed plural times.<br>(for adjustment of the film thickness and inhibition of pinhole generation) | Time: 1 to 60 seconds, preferably 10 to 45 seconds | continued on A |
| (d) Gelling step | Leave a cured film precursor thus obtained in the above-described step to stand under certain conditions so as to allow calcium ions to infiltrate into the cured film precursor and form crosslinked structures. | Without any humectant:<br>preferably at room temperature (about 23°C) for 20 seconds to 20 minutes, or at 50°C to 70°C for 20 seconds to 3 minutes.<br>With a humectant:<br>preferably at 50 to 70°C for less than 20 minutes, in addition to the above-described conditions. | |
| (e) Leaching step | Wash the resulting precured (preliminarily crosslinked) film with water to remove excess agents (elastomer, coagulant and the like). | Temperature: preferably 30 to 80°C<br>Time: preferably 30 seconds to 15 minutes | |
| (f) Beading step | Form a cuff | | |
| (g) Precuring step | The step of preliminarily heating the glove to warm the glove before crosslinking.<br>This step inhibits the generation of air bubbles in the film due to rapid boiling in the subsequent curing step. | Preferably performed at 60°C to 90°C for 30 seconds to 10 minutes. | |
| (h) Curing step | In this step, the carboxyl groups of the elastomer form crosslinks with carbodiimide, and $Zn^{2+}$ and/or $Al^{3+}$ substitute $Ca^{2+}$ and $NH_4^+$ to form crosslinks. The majority of the thus formed Ca crosslinks remain. | Temperature: preferably 70 to 140°C<br><br>Time: preferably 10 to 30 minutes | |

Fig.6-1

| | Steps | Differences in conditions between a glove having CDI crosslinks + Zn and/or Al crosslinks and a conventional glove, and special properties of crosslinks |
|---|---|---|
| A | (a) Coagulant adhesion step (step of preparing a glove mold to which a coagulant is adhered) | (1) Ca, which is a coagulant, is important for CDI crosslinking.<br>(2) Ca not only causes coagulation of XNBR in a dipping liquid, but also eventually forms Ca crosslinks in combination with multi-point crosslinking of a CDI. |
| | (b) Step of aging a dipping composition (step of preparing a dipping liquid in a tank) | (1) For CDI crosslinking, an ammonium compound or an amine compound is indispensable as a pH modifier.<br>(2) The ammonium compound or the amine compound forms salts with the carboxyl groups of the XNBR and is in an equilibrium state with -COOH.<br>When an aluminum compound is used, $-COO^-NH_4^+$ is converted back to -COOH due to evaporation of $NH_3$ in the curing step and is thereby allowed to react with the CDI.<br>On the other hand, with KOH used in ordinary XNBR gloves, the CDI crosslinking does not proceed. This is because $-COO^-K^+$ is not converted back to -COOH in the heat-curing (crosslinking) step. |
| | (c) Dipping step (step of immersing the glove mold in the dipping liquid and coagulating the XNBR on the glove mold) | (1) The coagulant, Ca, causes the XNBR to precipitate on the glove mold surface and to form a film. Ca is distributed toward the glove mold surface side of the resulting film.<br>(2) Since the system is aqueous, the CDI, which is protected by a hydrophilic segment, is dispersed in the film in an unreacted state. |
| | (d) Gelling step | (1) The $Ca^{2+}$ ions distributed toward the glove mold side in the dipping step infiltrate into the film during the gelling step and gradually substitute $-COO^-NH_4^+$ or amine salts, which exist in an equilibrium state with -COOH, into $-(COO^-)_2Ca^{2+}$; however, since excessive crosslinking with Ca leaves only a small amount of $-COO^-NH_4^+$ to react with the CDI in the curing step, it is important not to allow the reaction of Ca to proceed excessively.<br>(2) In order to prevent the above-described reaction of (1) from proceeding excessively due to activation of Ca at a high temperature, it is important not to perform the gelling step at a high temperature.<br>(3) Complete drying causes the hydrophilic segment of the CDI to open and the carbodiimide groups to be thereby exposed, bringing the CDI into a state of being available for reaction; however, since the temperature is not high enough to evaporate $NH_3$ and $-COO^-NH_4^+$ is thus not converted back to -COOH to become available for reaction, the CDI consequently reacts with water in the subsequent leaching step and thus cannot crosslink the XNBR. |
| | (e) Leaching step | (1) In this step, since $Ca^{2+}$ ions are removed by washing with water, the substitution of $-COO^-NH_4^+$ to $(-COO^-)_2Ca^{2+}$ is stopped.<br>(2) In addition, the pH is lowered in this step, so that complexes of Zn and Al are broken into $Zn^{2+}$ and $Al^{3+}$ ions, bringing these ions into a state of being available for reaction with -COOH. |
| | (f) Beading step | |
| | (g) Precuring step | |
| | (h) Curing step | (1) It is necessary that the hydrophilic segment of the CDI be opened and the carbodiimide groups be brought into a crosslinkable state at the same time, and that the conversion of $-COO^-NH_4^+$ back to -COOH also occur simultaneously.<br>(2) When the hydrophilic segment is opened without $-COO^-NH_4^+$ being converted back to -COOH, the carbodiimide groups react with residual water, so that the XNBR cannot be crosslinked. In this step, -COOH and carbodiimide groups react with each other to form N-acylurea structures, and some of $-COO^-NH_4^+$ and $(-COO^-)_2Ca^{2+}$ ions are eventually substituted with $Zn^{2+}$ and/or $Al^{3+}$ to form crosslinks. |

Fig.6-2

GLOVE DIPPING COMPOSITION, METHOD FOR MANUFACTURING GLOVES, AND GLOVES

CROSS-REFERENCE TO RELATED APPLICATION

The present disclosure is a national phase application of PCT Patent Application No. PCT/JP2017/045570 filed Dec. 19, 2017, which claims the priority benefit of Japanese Patent Application Nos. 2016-246008 filed Dec. 19, 2016 and 2016-247196 filed Dec. 20, 2016, the entire respective disclosures of which are incorporated herein by reference.

TECHNICAL FIELD

The present invention relates to: a glove dipping composition, a method of producing a glove; and a glove.

BACKGROUND ART

Conventionally, together with natural rubber gloves, rubber gloves obtained by crosslinking a carboxylated acrylonitrile-butadiene copolymer (XNBR) using sulfur as a crosslinking agent and a thiuram mix, a thiazole or the like as a sulfur-based vulcanization accelerator along with zinc oxide have been mainly used. Such gloves became the mainstream of the market because of their good performances; however, since sulfur-based vulcanization accelerators in particular cause type IV allergy, the development of a rubber glove obtained by non-sulfur crosslinking has been a theme. Yet, the use of a crosslinking agent containing neither sulfur nor a sulfur-based vulcanization accelerator does not yield sufficient performance in tensile strength, fatigue durability and the like as compared to XNBR gloves that are crosslinked using sulfur and a sulfur-based vulcanization accelerator.

There are cases where a polycarbodiimide is used as an organic crosslinking agent, aiming to produce a glove having performance that is comparable to or superior to that of a conventional sulfur-crosslinked XNBR glove.

Such cases of using a polycarbodiimide as an organic crosslinking agent include the following three technologies; however, it is believed that none of them has been completed in terms of practical application of a glove crosslinked with a polycarbodiimide.

Patent Document 1 discloses a method of producing a polycarbodiimide-crosslinked glove, and it is described therein that zinc oxide should be removed at the time of producing a glove.

In Patent Document 2, it is described that, although zinc oxide may be blended in a dip molding composition in which a polycarbodiimide is used as a crosslinking agent, it is rather preferred not to blend zinc oxide.

Patent Document 3 discloses to incorporate a carbodiimide as a crosslinkable compound and as an organic crosslinking agent in the polymerization of a carbodiimide-crosslinked glove and to add a carbodiimide as an organic crosslinking agent; however, since there are errors in the descriptions of the carbodiimide in the first place and potassium hydroxide is used as a pH modifier, it is believed that this technology cannot yield a carbodiimide-crosslinked glove. Further, although it is described that zinc oxide was added in Examples, the amount thereof and the reason for the addition are not described.

RELATED ART DOCUMENTS

Patent Documents

[Patent Document 1] Japanese Unexamined Patent Application Publication (Translation of PCT Application) No. 2015-513486

[Patent Document 2] Japanese Unexamined Patent Application Publication No. 2013-203914

[Patent Document 3] Korean Patent No. 10-1687866

SUMMARY OF THE INVENTION

Problems to be Solved by the Invention

According to the studies conducted by the present inventors, gloves produced by molding a glove dipping composition containing a polycarbodiimide as a crosslinking agent have the following drawbacks:

(1) such gloves were observed with a phenomenon of being swollen by long-term immersion in an artificial sweat solution as well as a phenomenon of rapid reduction in tensile strength after the immersion; and (2) such gloves were found to be inferior to sulfur-based XNBR gloves in terms of organic solvent impermeability.

In view of the above, an object of the present invention is to make improvements on the above-described two drawbacks by using a combination of a polycarbodiimide and other crosslinking agent. Another object of the present invention is to produce a glove that is comparable to a conventional sulfur-based XNBR glove having a good balance of various glove performances while reducing the amount of the crosslinking agents to be added as much as possible.

Means for Solving the Problems

In the present invention, as a means for solving the above-described problems, a specific amount of a polycarbodiimide is used as a crosslinking agent along with a specific amount of zinc oxide and/or an aluminum complex as a crosslinking agent(s) of an elastomer. Specifically, embodiments of the present invention relate to the following glove dipping composition, method of producing a glove, and glove.

[1] A glove dipping composition including, at least: an elastomer that contains a (meth)acrylonitrile-derived structural unit, an unsaturated carboxylic acid-derived structural unit and a butadiene-derived structural unit in a polymer main chain; a polycarbodiimide; zinc oxide and/or an aluminum complex; water; and at least one pH modifier selected from an ammonium compound and an amine compound, wherein the elastomer contains the acrylonitrile or methacrylonitrile-derived structural unit in an amount of 20 to 40% by weight, the unsaturated carboxylic acid-derived structural unit in an amount of 1 to 10% by weight, and the butadiene-derived structural unit in an amount of 50 to 75% by weight, the polycarbodiimide includes at least one polycarbodiimide containing a hydrophilic segment in its molecular structure, the polycarbodiimide has an average polymerization degree of 3.8 or higher and a carbodiimide equivalent of 260 to 600 and is added in an amount of 0.1 to 4.0% by weight with respect to the total solid content of the glove dipping composition, zinc oxide and/or the aluminum complex is added in an amount of 0.1 to 5.6% by weight with respect to the total solid content of the glove dipping composition, and the glove dipping composition has a pH of 9.0 to 11.5.

[2] The glove dipping composition according to [1], wherein the dipping composition contains zinc oxide, and the amount thereof is 0.1 to 4.0% by weight with respect to the total solid content of the glove dipping composition.

[3] The glove dipping composition according to [1], wherein the dipping composition contains zinc oxide and the aluminum complex, and the total amount thereof is 0.1 to 5.6% by weight with respect to the total solid content of the glove dipping composition.

[4] The glove dipping composition according to any one of [1] to [3], further containing a humectant.

[5] A method of producing a glove, the method including:

(1) the step of immersing a glove forming mold in a liquid coagulant containing calcium ions so as to allow the coagulant to adhere to the glove forming mold;

(2) the step of leaving the glove dipping composition according to any one of [1] to [3] to stand with stirring;

(3) the dipping step of immersing the glove forming mold, to which the coagulant has thus adhered in the step (1), in the glove emulsion composition;

(4) the gelling step of leaving the glove forming mold, to which the glove dipping composition has thus adhered, to stand at a temperature for a period that satisfy the following conditions:

conditions: a temperature and a period that allow the calcium ions contained in the coagulant to infiltrate into the elastomer contained in the glove dipping composition and to thereby induce gelation, without causing ammonium salts or amine salts of the elastomer contained in the glove dipping composition to be converted back to carboxyl groups and without causing the hydrophilic segment of the polycarbodiimide to be opened;

(5) the leaching step of removing impurities from a cured film precursor thus formed on the glove forming mold;

(6) the beading step of, after the leaching step, winding the cuff portion of the resulting glove;

(7) the precuring step of heating and drying the cured film precursor that has been subjected to the beading step; and (8) the curing step of heating the cured film precursor to obtain a cured film, the heating being performed at such a temperature for such a period that are sufficient for the ammonium salts or amine salts of the elastomer to be converted back to carboxyl groups, the carbodiimide groups of the polycarbodiimide to be exposed, and the carboxyl groups of the elastomer to react with the carbodiimide groups, which steps (3) to (8) are performed in the order mentioned.

[6] The method of producing a glove according to [5], wherein the glove dipping composition in the step (2) contains a humectant, and the conditions of the gelling step of (4) are: at 50 to 70° C. for 20 seconds to less than 20 minutes.

[7] The method of producing a glove according to [5], wherein the glove dipping composition in the step (2) contains no humectant, and the conditions of the gelling step of (4) are: at 15 to 25° C. for 20 seconds to 20 minutes, or at 50 to 70° C. for 20 seconds to less than 3 minutes.

[8] The method of producing a glove according to any one of [5] to [7], wherein the gelling step of (4) is performed under a condition of 40 to 60% RH.

[9] A glove produced by the method according to any one of [5] to [8], wherein the glove has the following performances:

(1) a fatigue durability of 200 minutes or longer; and (2) a tensile strength of 20 MPa or higher.

Effects of the Invention

A glove dipping composition from which a glove that exhibits only a small change in fatigue durability before and after being immersed in an artificial sweat solution and has excellent organic solvent impermeability can be formed even without the use of a conventional sulfur-based crosslinking agent; a glove having the above-described properties; and a method of producing the glove can be provided.

BRIEF DESCRIPTION OF THE DRAWINGS

FIG. 6-1 describes one example of the method of producing a glove according to one embodiment of the present invention.

FIG. 6-2 is a continuation of FIG. 6-1.

MODE FOR CARRYING OUT THE INVENTION

1. Glove Dipping Composition

Figure 1:
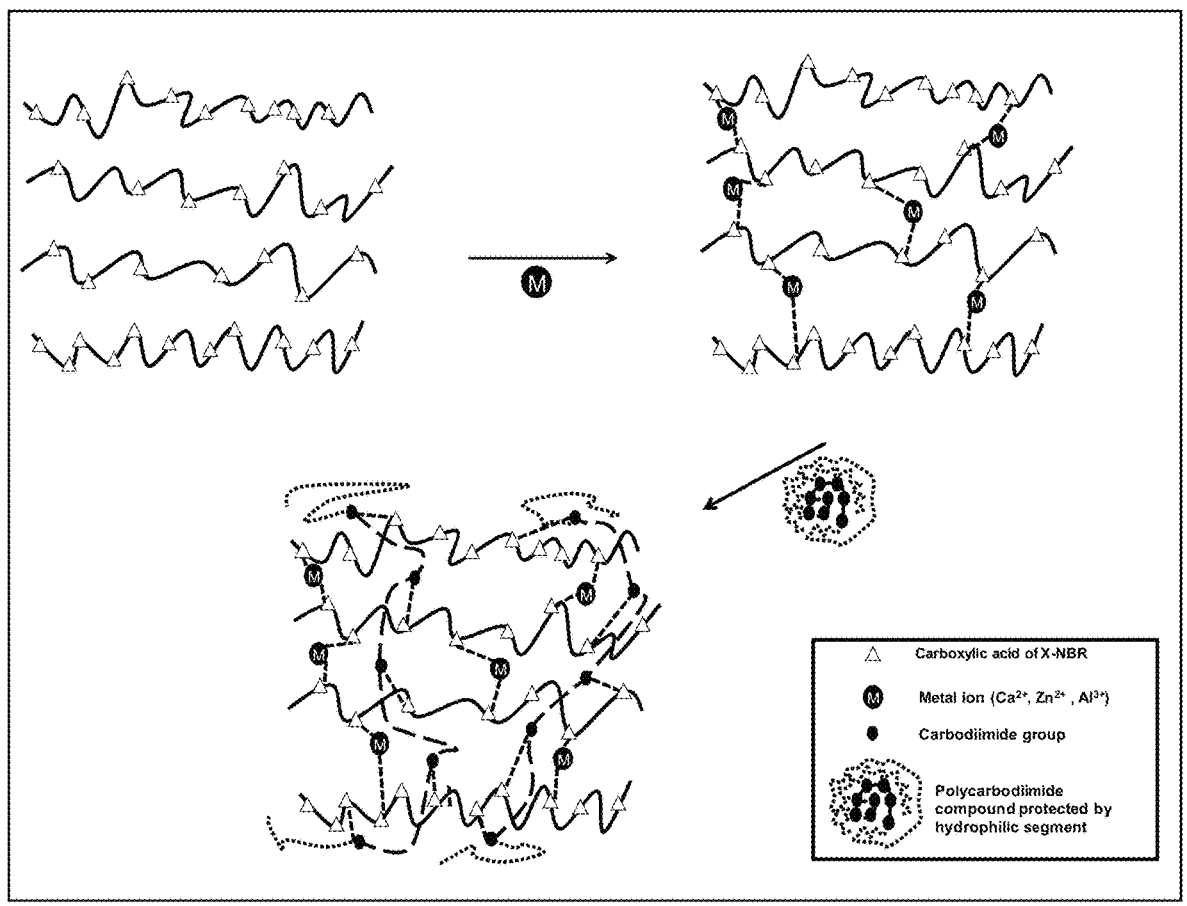
FIG. 1 is a conceptual diagram illustrating crosslinked structures that are believed to be contained in the glove according to one embodiment of the present invention, in which carboxyl groups of an XNBR are crosslinked at multiple points by a polycarbodiimide, and the carboxyl groups of the XNBR that are adjacent to each other are crosslinked by metal ions.

The glove according to one embodiment of the present invention is obtained by molding a dipping composition having the following formulation in accordance with the below-described production method.

The dipping composition includes, at least: an elastomer that contains a (meth)acrylonitrile-derived structural unit, an unsaturated carboxylic acid-derived structural unit and a butadiene-derived structural unit in a polymer main chain; a polycarbodiimide; zinc oxide and/or an aluminum complex; water; and at least one pH modifier selected from an ammonium compound and an amine compound.

The above-described components will now each be described below.

<Elastomer Containing (Meth)Acrylonitrile-Derived Structural Unit, Unsaturated Carboxylic Acid-Derived Structural Unit and Butadiene-Derived Structural Unit in Polymer Main Chain>

The elastomer used in the embodiments of the present invention contains, at least, a (meth)acrylonitrile-derived structural unit, an unsaturated carboxylic acid-derived structural unit and a butadiene-derived structural unit. This elastomer used in the embodiments of the present invention may also be hereinafter referred to as "carboxylated (meth) acrylonitrile-butadiene elastomer", or simply as "XNBR". The term "(meth)acrylonitrile" is a concept that encompasses both "acrylonitrile" and "methacrylonitrile".

With regard to the ratios of these structural units, the elastomer used in the embodiments of the present invention preferably contains: the (meth)acrylonitrile-derived structural unit, namely a (meth)acrylonitrile residue, in a range of 20 to 40% by weight; the unsaturated carboxylic acid-derived structural unit, namely an unsaturated carboxylic acid residue, in a range of 1 to 10% by weight; and the butadiene-derived structural unit, namely a butadiene residue, in a range of 50 to 75% by weight.

The ratios of these structural units can be simply determined from the weight ratios (solid content ratios) of the respective raw materials used for the production of the elastomer used in the embodiments of the present invention.

The (meth)acrylonitrile-derived structural unit is an element that mainly imparts strength to a rubber glove, and an excessively small amount thereof leads to insufficient strength, whereas an excessively large amount thereof improves the chemical resistance but makes the rubber glove overly hard. The ratio of the (meth)acrylonitrile-derived structural unit in the elastomer used in the embodiments of the present invention is more preferably 25 to 35% by weight. The amount of the (meth)acrylonitrile-derived structural units can be determined by converting the amount of nitrogen atoms, which is determined by elemental analysis, into the amount of nitrile groups.

The butadiene-derived structural unit is an element that imparts flexibility to a rubber glove and, usually, the flexibility is lost when the ratio of this structural unit is lower than 50% by weight. In the elastomer used in the embodiments of the present invention, the ratio of the butadiene-derived structural unit is preferably 65 to 72% by weight.

In order to maintain the physical properties of a rubber glove as a final product having an appropriate amount of crosslinked structures, in the elastomer used in the embodiments of the present invention, the amount of the unsaturated carboxylic acid-derived structural units is preferably 1 to 10% by weight, more preferably 1 to 9% by weight, particularly preferably 2 to 6% by weight. The amount of the unsaturated carboxylic acid-derived structural unit can be determined by quantifying carboxyl groups and carbonyl groups derived from carboxyl groups by infrared (IR) spectroscopy or the like. The carboxyl groups of the unsaturated carboxylic acid-derived structural units form crosslinked structures with the below-described polycarbodiimide, calcium, and zinc oxide and/or aluminum complex.

The unsaturated carboxylic acid forming the unsaturated carboxylic acid-derived structural unit is not particularly restricted, and may be a monocarboxylic acid or a polycarboxylic acid. More specific examples of the unsaturated carboxylic acid include acrylic acid, methacrylic acid, crotonic acid, maleic acid, and fumaric acid. Thereamong, acrylic acid and/or methacrylic acid (hereinafter, collectively referred to as "(meth)acrylic acid") is preferably used, and methacrylic acid is more preferably used.

The butadiene-derived structural unit is preferably a structural unit derived from 1,3-butadiene.

It is preferred that the polymer main chain be substantially constituted by the (meth)acrylonitrile-derived structural unit, the unsaturated carboxylic acid-derived structural unit and the butadiene-derived structural unit; however, the polymer main chain may also contain a structural unit derived from other polymerizable monomer.

In the elastomer used in the embodiments of the present invention, the structural unit derived from other polymerizable monomer is contained in an amount of preferably not greater than 30% by weight, more preferably not greater than 20% by weight, still more preferably not greater than 15% by weight.

Examples of other polymerizable monomers that can be preferably used include aromatic vinyl monomers, such as styrene, α-methylstyrene and dimethyl styrene; ethylenically unsaturated carboxylic acid amides, such as (meth) acrylamide and N,N-dimethylacrylamide; ethylenically unsaturated carboxylic acid alkyl ester monomers, such as methyl (meth)acrylate, ethyl (meth)acrylate, butyl (meth) acrylate and 2-ethylhexyl (meth)acrylate; and vinyl acetate. These monomers may be used alone, or in combination of two or more thereof as desired.

The elastomer used in the embodiments of the present invention can be prepared by emulsion-polymerizing, in accordance with a conventional method, an unsaturated carboxylic acid (e.g., (meth)acrylonitrile or (meth)acrylic acid), a butadiene (e.g., 1,3-butadiene) and, as required, other polymerizable monomer(s), using an emulsifying agent, a polymerization initiator, a molecular weight modifier and the like that are normally used. In this emulsion polymerization, water is incorporated in such an amount that attains a solid content of preferably 30 to 60% by weight, more preferably 35 to 55% by weight.

After the synthesis of the elastomer used in the embodiments of the present invention, the resulting emulsion polymerization solution can be directly used as an elastomer component of the dipping composition.

Examples of the emulsifying agent include anionic surfactants, such as dodecylbenzenesulfonates and aliphatic sulfonates; cationic sulfonates, such as polyethylene glycol alkyl ethers and polyethylene glycol alkyl esters; and amphoteric surfactants, and an anionic surfactant is preferably used.

The polymerization initiator is not particularly restricted as long as it is a radical initiator, and examples thereof include inorganic peroxides, such as ammonium persulfate and potassium superphosphate; organic peroxides, such as t-butyl peroxide, cumene hydroperoxide, p-menthane hydroperoxide, di-t-butyl peroxide, t-butylcumyl peroxide, dibenzoyl peroxide, 3,5,5-trimethylhexanoyl peroxide, and t-butyl peroxyisobutyrate; and azo compounds, such as azobisisobutyronitrile, azobis-2,4-dimethyl valeronitrile, azobiscyclohexane carbonitrile, and methyl azobisisobutyrate.

Examples of the molecular weight modifier include mercaptans, such as t-dodecylmercaptan and n-dodecylmercaptan; and halogenated hydrocarbons, such as carbon tetrachloride, methylene chloride and methylene bromide, among which mercaptans such as t-dodecylmercaptan and n-dodecylmercaptan are preferred.

The Mooney viscosity ($ML_{(1+4)}$ (100° C.)) of the elastomer used in the embodiments of the present invention is a factor that greatly affects the tensile strength of a glove;

however, in the embodiments of the present invention, the Mooney viscosity of the elastomer is not particularly restricted.

The Mooney viscosity of the elastomer used in the embodiments of the present invention may be, for example, about 70 or higher, and the upper limit thereof is, for example, about 160. The reason for this is that, as seen from the below-described results shown in Table 6 and FIG. 3, an excessively high Mooney viscosity of the elastomer tends to deteriorate the fatigue durability.

Meanwhile, the tensile strength of the glove according to one embodiment of the present invention can be adjusted by increasing the amount of the below-described zinc oxide and or aluminum complex to be incorporated into the dipping composition; however, with this amount being constant, a higher Mooney viscosity of the elastomer used in the embodiments of the present invention tends to impart the resulting glove with a higher tensile strength.

For instance, when the zinc oxide content in the dipping composition is 0.5% by weight and the elastomer according to one embodiment of the present invention has a Mooney viscosity of 70, a tensile strength required for a glove, which is 20 MPa, can be ensured; therefore, in the present invention, it is believed that the Mooney viscosity of the XNBR is suitably in a range of 70 to 160.

The lower the amount of gel fraction in the elastomer used in the embodiments of the present invention, the more preferred it is. This is because, in order to allow the polycarbodiimide, which has a higher molecular weight than zinc oxide and sulfur, to be easily incorporated into the polymer chain, it is appropriate that the polymer chain have only a small amount of branches and be linear.

Accordingly, as a method of producing the elastomer (XNBR) used in the embodiments of the present invention, cold rubber production (polymerization temperature: 5 to 25° C.) is more preferred than hot rubber production (polymerization temperature: 25 to 50° C.).

The methyl ethyl ketone (MEK)-insoluble content is preferably 40% by weight or less, particularly preferably 10% by weight or less.

The amount of the elastomer (XNBR) contained in the glove dipping composition according to one embodiment of the present invention is, for example, 15 to 35% by weight, preferably 18 to 30% by weight, in terms of solid content.

<Polycarbodiimide, Zinc Oxide and/or Aluminum Complex>

The glove dipping composition according to one embodiment of the present invention contains a polycarbodiimide, and zinc oxide (hereinafter, also referred to as "ZnO") and/or an aluminum complex (hereinafter, also referred to as "Al complex") as crosslinking agents.

These crosslinking agents are each described below.

(1) Polycarbodiimide

The polycarbodiimide used in the embodiments of the present invention is constituted by a core moiety that undergoes a crosslinking reaction with carboxyl groups, and a hydrophilic segment added to a terminal of the core moiety. Further, some of terminals may be capped with a capping agent.

<Core Moiety of Polycarbodiimide>

First, the chemical formula of the core moiety of the polycarbodiimide used in the embodiments of the present invention is shown below.

$$\text{NCO—}(R^1\text{—}(N{=}C{=}N)\text{-})m\text{-}R^1\text{OCN} \tag{1}$$

In this Formula (1), —N=C=N— is a carbodiimide group that reacts with a carboxyl group of the XNBR.

The m is an integer of 4 to 20 and indicates the polymerization degree.

By controlling the m to be 4 or higher, the polycarbodiimide can crosslink the carboxyl groups of the elastomer (XNBR) used in the embodiments of the present invention at multiple points and the elastomer (XNBR) used in the embodiments of the present invention is consequently integrated in a lump, and this is believed to be the reason why very good fatigue durability is attained as compared to a case of using a two-point crosslinking agent.

The core moiety of the polycarbodiimide is usually generated by decarboxylation condensation of a diisocyanate and has an isocyanate residue on both terminals. In the above-described formula, both terminals are shown as isocyanate groups. The diisocyanate can be, for example, an aromatic diisocyanate, aliphatic diisocyanate, an alicyclic diisocyanate, or a mixture thereof. Specific examples thereof include 1,5-naphthylene diisocyanate, 4,4-diphenylmethane diisocyanate, 4,4-diphenyldimethylmethane diisocyanate, 1,3-phenylene diisocyanate, 1,4-phenylene diisocyanate, 2,4-tolylene diisocyanate, 2,6-tolylene diisocyanate, a mixture of 2,4-tolylene diisocyanate and 2,6-tolylene diisocyanate, hexamethylene diisocyanate, cyclohexane-1,4-diisocyanate, xylylene diisocyanate, isophorone diisocyanate, dicyclohexylmethane-4,4-diisocyanate, methylcyclohexane diisocyanate, and tetramethylxylylene diisocyanate. From the standpoint of the weather resistance, it is preferred to incorporate a polycarbodiimide generated by a condensation reaction involving decarboxylation of an aliphatic or alicyclic diisocyanate. One representative type of the diisocyanate is dicyclohexylmethane-4,4'-diisocyanate.

<Hydrophilic Segment>

Carbodiimide groups readily react with water; therefore, in the glove dipping composition according to one embodiment of the present invention, in order to protect the carbodiimide groups from water such that their reactivity with the elastomer (XNBR) used in the embodiments of the present invention is not lost, it is indispensable that a hydrophilic segment be added to a terminal (isocyanate group) in some of the polycarbodiimide molecules.

The following Formula (2) shows the structure of the hydrophilic segment.

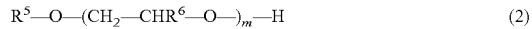

$$R^5\text{—O—}(CH_2\text{—}CHR^6\text{—O—})_m\text{—H} \tag{2}$$

In the Formula (2), $R^5$ is an alkyl group having 1 to 4 carbon atoms, $R^6$ is a hydrogen atom or a methyl group, and m is an integer of 5 to 30.

In the glove dipping composition (dipping liquid/water), the hydrophilic segment functions to protect carbodiimide groups by surrounding the core moiety of the polycarbodiimide that readily reacts with water (shell-core structure).

Meanwhile, drying causes the hydrophilic segment to open, thereby creating a state where the carbodiimide groups are exposed and thus available for reaction. Therefore, in the glove production by dip molding according to the present invention, it is important not to dry the glove dipping composition until the final heat-crosslinking (curing) step where the carbodiimide groups react with the carboxyl groups of the elastomer (XNBR) used in the embodiments of the present invention and to thereby avoid the reaction with water, which is different from a case of using a coating material. For this purpose, it is also effective to add the below-described humectant to the glove dipping composition.

The hydrophilic segment may be coordinated on both or either one of the terminals of the core moiety. Further, a mixture of a polycarbodiimide having a hydrophilic segment and a polycarbodiimide having no hydrophilic segment may be used as well.

The terminal that has no hydrophilic segment added thereto is capped with a capping agent.

The capping agent is represented by the following Formula (3).

$$(R')_2\text{-N}-R^2-\text{OH} \qquad (3)$$

In this Formula (3), $R^1$ is an alkyl group having not more than 6 carbon atoms and, from the availability standpoint, $R^1$ is preferably an alkyl group having not more than 4 carbon atoms. $R^2$ is an alkylene, polyalkylene or oxyalkylene group having 1 to 10 carbon atoms.

<Polymerization Degree, Molecular Weight, and Equivalent>

The average polymerization degree (number-average molecular weight/carbodiimide equivalent) of the polycarbodiimide is 3.8 or higher, preferably 4 or higher, more preferably 9 or higher. Such an average polymerization degree is required for appropriately forming multi-point crosslinked structures, which is a characteristic feature of the glove according to one embodiment of the present invention, and thereby imparting the glove with high fatigue durability.

The molecular weight of the polycarbodiimide is preferably 500 to 5,000, more preferably 1,000 to 4,000, in terms of number-average molecular weight.

The number-average molecular weight can be measured as follows by a GPC method (calculated in terms of polystyrene).

RI detector: RID-6A (manufactured by Shimadzu Corporation)

Columns: KF-806, KF-804L, and KF-804L (manufactured by Showa Denko K.K.)

Developing solvent: THF 1 ml/min

As for the carbodiimide equivalent, when the polycarbodiimide is added in an amount of 3% by weight, the fatigue durability exceeds 1,500 minutes in an equivalent range of 260 to 600. However, when the polycarbodiimide is added in an amount of 1% by weight, an equivalent of 440 or higher leads to a considerably low fatigue durability of 100 minutes or shorter. Accordingly, the carbodiimide equivalent is preferably in a range of 260 to 440. It is noted here that the lower limit value of the carbodiimide equivalent is in a range that yields a product.

The carbodiimide equivalent is a value calculated using the following equation (I) from the carbodiimide group concentration measured by back titration with oxalic acid:

$$\text{Carbodiimide equivalent} = \text{Number of carbodiimide groups } (40) \times 100/\text{Carbodiimide group concentration } (\%) \qquad (I)$$

In the glove dipping composition according to one embodiment of the present invention, the polycarbodiimide is added in an amount of, for example, 0.1 to 4.0% by weight, preferably 0.1 to 2.5% by weight, more preferably 0.3 to 2.0% by weight, with respect to the solid content of the glove dipping composition. With regard to the range of this amount, it has been verified that, while the fatigue durability is reduced when the amount is greater than 7.0 parts by weight, even a relatively small amount of 0.5 parts by weight can impart the resulting glove with fatigue durability superior to those of other sulfur-based gloves.

(2) Zinc Oxide and/or Aluminum Complex

In the present invention, zinc oxide and/or an aluminum complex is/are used in combination with the polycarbodiimide to perform crosslinking, whereby swelling and a reduction in the tensile strength of a glove obtained from the glove dipping composition in an artificial sweat solution can be inhibited and the organic solvent impermeability is improved.

(A) Zinc Oxide (ZnO)

In a preferred embodiment of the present invention, in addition to the polycarbodiimide, by adding a small amount of zinc oxide to the glove dipping composition, swelling and a reduction in the tensile strength of a glove obtained from the glove dipping composition in an artificial sweat solution can be inhibited and the organic solvent impermeability is improved.

The zinc oxide used in this embodiment of the present invention is not particularly restricted, and any commonly used zinc oxide can be used.

It is noted here that the content of zinc oxide has a proportional relationship with the initial tensile strength of the resulting glove and that, therefore, the strength of the glove can be adjusted by changing the content of zinc oxide. Particularly, in the production of a thin glove, the strength can be maintained by increasing the amount of zinc oxide.

The crosslinking reaction of zinc oxide is described below.

Zinc oxide is added at the time of preparing the glove dipping composition and, since zinc oxide is negatively charged forming complexes $[Zn(OH)_4]^{2-}$, zinc oxide does not form a salt with a carboxyl group of the elastomer contained in the glove dipping composition.

However, in the leaching step of the below-described method of producing a glove, a reduction in pH causes the complexes to break and release $Zn^{2+}$ ions, and the carboxyl groups of the elastomer are crosslinked by the $Zn^{2+}$ ions via ionic bonds in the curing step of the below-described method of producing a glove.

In the glove dipping composition according to one embodiment of the present invention, zinc oxide is usually added in an amount of, for example, 0.1 to 4.0% by weight, preferably 0.1 to 2.5% by weight, more preferably 0.3 to 2.0% by weight, with respect to the total solid content of the glove dipping composition. In order to solve the above-described problems, the amount of zinc oxide to be added in the glove according to one embodiment of the present invention may be smaller than the amount added in a conventional ordinary glove, which is, for example, about 0.25% by weight.

It is noted here that the lower limit value of 0.1% by weight assumes a case where zinc oxide is incorporated alone, and zinc oxide may be added in a smaller amount when the glove dipping composition contains both zinc oxide and an aluminum complex.

(B) Aluminum Complex

As the aluminum complex, one prepared by the present inventors as a trial based on a prior art document (Chiba Industrial Technology Research Institute Report No. 8, p. 22 to 27, 2010) can be used.

The method of synthesizing an aluminum complex used in one embodiment of the present invention is described below. In the below-described Examples, an aluminum citrate complex, an aluminum malate complex and an aluminum hydroxide complex were prepared and examined by experiments. As a result, the aluminum hydroxide complex was found to contribute the most to the properties of a glove; however, good properties can be attained even when other aluminum complex is used.

In a preferred embodiment of the present invention, in addition to the polycarbodiimide, by adding a small amount of an aluminum complex to the glove dipping composition, swelling and a reduction in the tensile strength of a glove obtained from the glove dipping composition in an artificial sweat solution can be inhibited and the organic solvent impermeability is improved. An aluminum complex is use for substantially the same purposes as those of zinc oxide described above.

An aluminum complex, however, is much more difficult to handle than zinc oxide and, as compared to zinc oxide, it is more difficult to allow a large amount of an aluminum complex to undergo a crosslinking reaction. In the glove according to one embodiment of the present invention, an aluminum complex has a greater effect of improving the organic solvent impermeability than zinc oxide, and a higher tensile strength is attained by using an aluminum oxide for crosslinking as compared to a case of using zinc oxide at the same amount. On the other hand, when aluminum is added to the glove in an excessively large amount, the hardness of the glove is increased.

Taking these points into account, the amount of an aluminum complex to be added in the glove dipping composition according to one embodiment of the present invention is, in terms of the amount of aluminum oxide ($Al_2O_3$) preferably 0.1 to 1.6% by weight, more preferably 0.1 to 1.4% by weight, still more preferably 0.2 to 1.0% by weight, with respect to the total solid content of the glove dipping composition. It is noted here that the lower limit value of 0.1% by weight assumes a case where an aluminum complex is incorporated alone, and an aluminum complex may be added in a smaller amount when the glove dipping composition contains both zinc oxide and an aluminum complex.

Similarly to zinc oxide, an aluminum complex is added to the glove dipping composition according to one embodiment of the present invention. In the leaching step of the below-described method of producing a glove, the complex is broken into $Al^{3+}$ ions, and the carboxyl groups of the elastomer contained in the glove dipping composition are crosslinked by the $Al^{3+}$ ions via ionic bonds in the curing step of the below-described method of producing a glove.

(C) Combination of Zinc Oxide and Aluminum Complex

In the glove dipping composition according to one embodiment of the present invention, in addition to the polycarbodiimide, a combination of zinc oxide and an aluminum complex may be added as well. As shown by the results of the below-described Examples, a reduction in tensile strength in an artificial sweat solution and the organic solvent impermeability can be improved by using zinc oxide and an aluminum complex in combination with the polycarbodiimide; however, an aluminum complex is superior to zinc oxide in terms of improving the initial tensile strength and the above-described two properties.

On the other hand, an aluminum complex has drawbacks in that it is difficult to increase the amount of thereof to be added and that an aluminum complex is likely to cause an increase in hardness.

Therefore, by using zinc oxide and an aluminum complex in combination, their drawbacks are suppressed and their merits can be attained.

Further, according to the below-described Examples, unexpected results indicating that a combination of these materials also improves the fatigue durability were obtained.

When both zinc oxide and an aluminum complex are incorporated into the glove dipping composition according to one embodiment of the present invention, the range of the amount of zinc oxide and the aluminum complex to be added is, for example, the respective ranges exemplified above for each material, and a preferred range is also the same. Zinc oxide and the aluminum complex are added in a total amount of, for example, 0.1 to 5.6% by weight, preferably 0.5 to 3.5% by weight, with respect to the total solid content of the dipping composition.

(3) pH Modifier

In the glove dipping composition according to one embodiment of the present invention, as a pH modifier for adjusting the pH to 9 to 11.5, it is indispensable to use an ammonium compound such as ammonia or ammonium hydroxide, or an amine compound. The ammonium compound or the amine compound forms ammonium salts or amine salts with the carboxyl groups of the elastomer (XNBR); however, due to evaporation and separation of ammonia or the like caused by heating in the curing step, these salts are converted back to the carboxyl groups (—COOH) and react with the polycarbodiimide (CDI). That is, the ammonium compound or the amine compound plays a role in securing a place for the reaction of the polycarbodiimide.

Meanwhile, in the case of potassium hydroxide that is normally used as a pH modifier is used, although it forms —COO$^-$K$^+$, it cannot react with the polycarbodiimide since potassium is not evaporated and —COO$^-$K$^+$ is thus not converted back to (—COOH).

The pH modifier is usually used in an amount of 0.1 to 5.0% by weight or so with respect to the total solid content of the glove dipping composition.

As described above, the pH of the glove dipping composition is adjusted with the pH modifier. That is, in order to allow both the below-described crosslinking between carboxyl groups by calcium ions of a coagulant and the crosslinking by the polycarbodiimide to proceed smoothly, the pH of the glove dipping composition is 9 or higher, preferably 9.5 or higher, more preferably 10 or higher. Meanwhile, from the standpoint of the ease of adjustment, the pH of the glove dipping composition is preferably 11.0 or lower, more preferably 10.5 or lower.

(4) Humectant

The glove dipping composition according to one embodiment of the present invention preferably contains a humectant.

When a humectant is contained in the glove dipping composition, in the below-described method of producing a glove by dip molding, the hydrophilic segment of the polycarbodiimide can be prevented from opening due excessive dying prior to the precuring step.

Examples of the humectant include polyols, among which a divalent or trivalent compound is preferably used. Specifically, examples of the divalent compound include ethylene glycol, propylene glycol, tetramethylene glycol, diethylene glycol, dipropylene glycol and polyethylene glycol, and examples of the trivalent compound include glycerol. Thereamong, the glove dipping composition preferably contains glycerol as the humectant.

The amount of the humectant to be used is, for example, 1.0 to 5.0 parts by weight or so, preferably 1.5 to 3.0 parts by weight, with respect to 100 parts by mass of the elastomer contained in the glove dipping composition.

In addition to the functions as a humectant, the above-described humectant is believed to also play a role in securing the carboxyl groups to be crosslinked with the polycarbodiimide by forming coordinate bonds with $Ca^{2+}$ in the gelling step and thereby inhibiting substitution of ammonium salts of the carboxyl groups to Ca salts.

The glove dipping composition contains at least the above-described indispensable components and water and, in addition thereto, the glove dipping composition usually contains other optional components.

For example, a mode of preparing the glove dipping composition such that the crosslinked structures of the resulting glove consist of crosslinked structures formed by the polycarbodiimide, crosslinked structures formed by calcium ions originating from the coagulant and crosslinked structures formed by $Zn^{2+}$ and/or $Al^{3+}$ originating from zinc oxide and/or an aluminum complex may be adopted.

The glove dipping composition may also contain a dispersant. The dispersant is preferably an anionic surfactant, and examples thereof include carboxylates, sulfonates, phosphates, polyphosphates, high-molecular-weight alkyl aryl sulfonates, high-molecular-weight sulfonated naphthalenes and high-molecular-weight naphthalene/formaldehyde condensation polymers, among which a sulfonate is preferably used.

As the dispersant, a commercially available product may be used. For example, TAMOL NN9104 can be used. The amount thereof to be used is preferably 0.5 to 2.0 parts by weight or so with respect to 100 parts by mass of the elastomer contained in the glove dipping composition.

The glove dipping composition may further contain a variety of other additives. Examples of the additives include an antioxidant, a pigment, and a chelating agent. As the antioxidant, a hindered phenol-type antioxidant, such as WINGSTAY L, can be used. Further, as the pigment, for example, titanium dioxide can be used. As the chelating agent, sodium ethylenediaminetetraacetate or the like can be used.

The glove dipping composition according to the present embodiment can be prepared by mixing the above-described elastomer, polycarbodiimide, zinc oxide and/or aluminum complex and pH modifier along with, as required, various additives such as a humectant, a dispersant and an antioxidant, and water using a commonly-used mixing means, such as a mixer.

2. Method of Producing Glove

The method of producing a glove according to one embodiment of the present invention is largely different from a conventional glove production method where sulfur and zinc are used as crosslinking agents and an XNBR is used as an elastomer.

In the glove according to one embodiment of the present invention, since a polycarbodiimide is used as a crosslinking agent in place of a sulfur vulcanization agent, an ammonium compound or an amine compound is indispensable as a pH modifier for the preparation of a glove dipping composition. Further, among the steps of the production method, particularly the gelling step requires different conditions.

<Steps Included in Method of Producing Glove According to the Present Invention>

Figure 2:
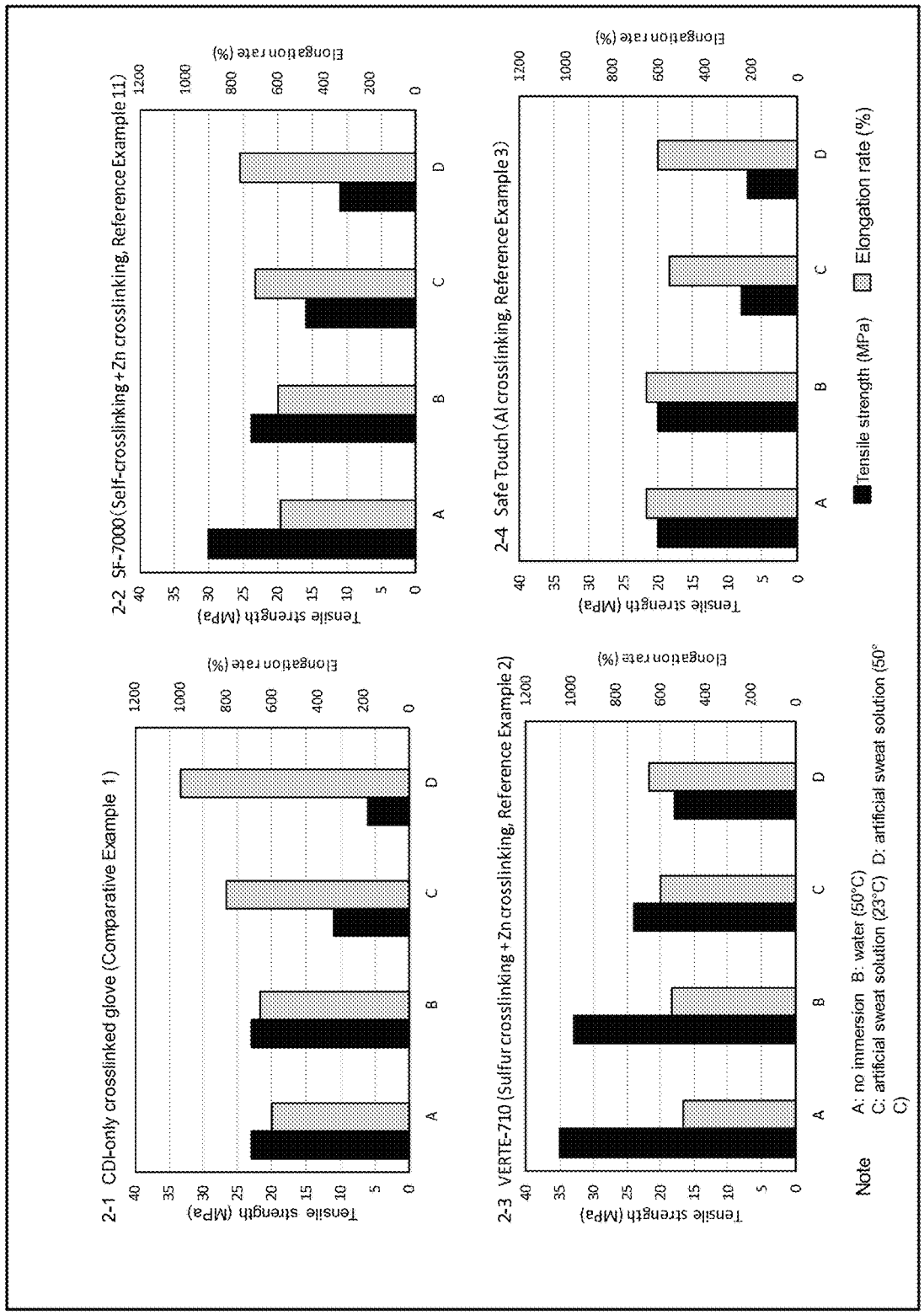
FIG. 2 provides graphs showing the changes in tensile strength and elongation of various gloves before and after a 20-hour immersion test (at normal temperature and 50° C.) performed in water and artificial sweat solutions for each glove.

A concrete embodiment of the method of producing a glove according to the present invention is exemplified in detail in FIGS. 6-1 and 6-2. The steps included in the method of producing a glove according to one embodiment of the present invention are each described below. The characteristic features thereof are that: in order to realize crosslinking by a polycarbodiimide in the below-described curing step (h), an ammonium compound or an amine compound is indispensable as a pH modifier; excessive substitution of ammonium salts or amine salts of an elastomer (XNBR) with Ca salts is suppressed in the below-described gelling step (d) so as to secure ammonium salts or amine salts that react with the polycarbodiimide to form crosslinks in the below-described curing step (h); and, a film (cured film precursor) formed on a glove forming mold is prevented from being dried such that a hydrophilic segment of the polycarbodiimide does not open until the below-described curing step (h). With regard to other points, a glove is produced by the same steps as in a conventional XNBR glove production method.

The characteristic features of the method of producing a glove according to one embodiment of the present invention are as described above, and a large difference from a common glove production method is the flow of the formation of polycarbodiimide crosslinks. Further, the present inventors examined the process of Ca crosslinking as well as the process of Zn crosslinking and/or Al crosslinking. In this respect, FIGS. 6-1 and 6-2 provide detailed descriptions.

In a preferred embodiment, a glove can be produced as follows. The steps will now each be described.

The following steps (a) and (b) correspond to the preparation of a continuous production line.

(a) Coagulant Adhesion Step

This is the step of immersing a mold or a former (glove forming mold) in a coagulant solution that contains a coagulant and $Ca^{2+}$ ions as a gelling agent in an amount of usually 5 to 40% by weight, preferably 8 to 35% by weight, and subsequently drying, at 50 to 70° C., the entirety or a part of the surface of the mold or the former to which the coagulant has thus adhered. In this step, the period of allowing the coagulant and the like to adhere to the surface of the mold or the former is determined as appropriate, and it is usually 10 to 20 seconds or so. As the coagulant solution, for example, an aqueous solution that contains 5 to 40% by weight of a coagulant such as calcium nitrate or calcium chloride, or a flocculant such as an inorganic salt having an effect of precipitating the elastomer, is used. It is preferred that the coagulant solution also contain potassium stearate, calcium stearate, a mineral oil, an ester-based oil or the like as a release agent in an amount of 0.5 to 2% by mass or so, for example, about 1% by weight.

The coagulant plays a role in causing the elastomer (XNBR) to aggregate in the dipping step. In addition, the coagulant is incorporated into the resulting glove in a large amount, forming crosslinks as calcium crosslinks.

In the present invention, adjustment of calcium crosslinking is an important point.

(b) Glove Dipping Composition Aging Step

This is the step of leaving the glove dipping composition with stirring. This step is also referred to as "aging" and can be performed for a period of, for example, 5 hours or longer, and it is preferred to perform the aging for at least 24 hours. Meanwhile, the period of performing the aging is preferably not longer than 72 hours. By performing the aging, the glove dipping composition can be prevented from becoming heterogeneous, and this contributes to imparting a uniform finish to the resulting glove. It is required that the glove dipping composition be adjusted with an ammonium compound or an amine compound to have a pH of 9.0 or higher, and the reactivity is reduced at a pH of lower than 9.0.

The following steps (c) to (h) constitute a continuous process.

(c) Dipping Step

The dipping step is the step of immersing the mold or the former, which has been dried in the step (a), in the glove dipping composition, for example, for a period of 1 to 60 seconds at a temperature of 25 to 35° C., and thereby allowing the glove dipping composition to adhere to the mold or the former to which the coagulant has adhered. In this dipping step, the calcium ions contained in the coagulant cause the elastomer in the glove dipping composition to aggregate on the surface of the mold or the former, whereby a film is formed. In this process, the carbodiimide groups of the polycarbodiimide are in a state of being protected by a hydrophilic segment.

As described above, it is required that the glove dipping composition be adjusted with a pH modifier, such as an ammonium compound (e.g., ammonia or ammonium hydroxide) or an amine compound, to have a pH of 9.0 or higher, and the reactivity is reduced at a pH of lower than 9.0. As a result of the adjustment, the carboxyl groups (—COOH) of the elastomer contained in the glove dipping composition form ammonium salts (—COO$^-$NH$_4^+$) or amine salts (—COO$^-$NHR$_3^+$, —COO$^-$NH$_2$R$_2^+$, —COO$^-$NH$_3$R+: hereinafter, the chemical formulae of the amine salts are abbreviated), and the thus formed salts exist in an equilibrium state with (—COOH). The R of the amine salts represents an organic group of the amine compound used as the pH modifier.

When zinc oxide is added to the glove dipping composition, zinc exists in the form of a zinc hydroxide complex in the glove dipping composition. When an organic aluminum complex is added, it exists in the form of an organic acid complex. These complexes are both negatively charged and, therefore, do not react with the carboxyl groups.

Further, in one embodiment of the present invention, as described above, a humectant may be incorporated into the glove dipping composition. By incorporating a humectant, in the step prior to the curing step that is the final step, opening of the hydrophilic segment of the polycarbodiimide caused by drying and thus deactivation of the polycarbodiimide before crosslinking can be prevented. In addition, even under a certain level of stringent drying conditions, the mold or the former to which the glove dipping composition has adhered can be prevented from being dried more than necessary, so that unnecessary crosslinking reaction does not take place before the final crosslinking between the polycarbodiimide and the elastomer (XNBR).

It is believed that the humectant exerts an effect of facilitating polycarbodiimide crosslinking by forming coordinate bonds with Ca$^{2+}$ ions and thereby inhibiting substitution of the ammonium salts of the carboxyl groups of the elastomer (XNBR) to calcium salts.

As the humectant, those exemplified above in relation to the glove dipping composition can be used.

(d) Gelling Step

The gelling step is the step of leaving the mold or the former, to which the glove dipping composition has adhered in the step (c), to stand under the below-exemplified conditions and thereby inhibiting elution of the elastomer in the subsequent leaching step. By performing this gelling step, the calcium ions contained in the coagulant infiltrate into the elastomer contained in the glove dipping composition, which elastomer is in a simple aggregated state on the surface of the mold or the former, and form crosslinked structures, so that elution of the elastomer does not occur in the subsequent leaching step.

The gelling step included in the embodiments of the method of producing a glove according to the present invention is performed under totally different conditions from those of a conventionally known gelling step that is performed in a glove production method where an elastomer is crosslinked through zinc oxide and sulfur.

First, in a conventional gelling step, an elastomer is crosslinked to a certain extent by heating and drying at a temperature of 80 to 120° C. and, after subsequently removing impurities by leaching, the resultant is further heated to allow reactions to take place between carboxyl groups contained in an elastomer and zinc as well as between a diene and sulfur.

In such a conventional glove production process, even if calcium and the elastomer are excessively crosslinked, the subsequent crosslinking is not affected as in the present invention; therefore, there is no problem in performing the gelling by drying at a high temperature of 80 to 120° C.

In contrast, in the method of producing a glove according to one embodiment of the present invention, the glove dipping composition is also gelled by the gelling step of allowing the calcium ions of the coagulant and the carboxyl groups of the elastomer to react with each other; however, there are several restrictions on the conditions of the gelling step as described below.

For example, in cases where calcium nitrate is used as the coagulant for gelling and the pH adjustment is performed using ammonia, the calcium ions contained in the coagulant react with (—COO$^-$NH$_4^+$) of the elastomer contained in the glove dipping composition to generate structures represented by ((—COO$^-$)$_2$Ca$^{2+}$) (hereinafter, also referred to as "(A)") and ammonium nitrate. The amount of (—COO$^-$NH$_4^+$) is reduced by the reaction with the calcium ions but supplemented by (—COOH) in an equilibrium state, so that the equilibrium state is maintained.

The (—COOH) and (—COO$^-$NH$_4^+$) are hereinafter collectively referred to as "(B)".

In cases where the pH adjustment is performed using an amine compound, the calcium ions of the coagulant react with amine salts of the elastomer. In cases where both ammonia and an amine compound are used as pH modifiers, the calcium ions of the coagulant react with both ammonium salts (—COO$^-$NH$_4^+$) and amine salts (—COO$^-$NHR$_3^+$) of the elastomer.

The glove according to one embodiment of the present invention contains, as described below, bonds formed by the carboxyl groups of the elastomer and calcium originating from the coagulant, bonds formed by the carboxyl groups of the elastomer and the carbodiimide groups of the polycarbodiimide, and bonds formed by the carboxyl groups of the elastomer and zinc ions and/or aluminum ions. The above-described (A) are, by curing, converted into bonds formed by the carboxyl groups and zinc and/or aluminum and bonds formed by the carboxyl groups and calcium. As for the above-described (B), some of the (—COO$^-$NH$_4^+$) salts form bonds with zinc and/or aluminum, while other salts form crosslinked structures with the polycarbodiimide.

In the gelling step, when the reaction between (—COO$^-$NH$_4^+$) and/or (—COO$^-$NHR$_3^+$) of the elastomer and the calcium ions overly proceeds, the ratio of (B) in the elastomer becomes excessively low, and this leads to a reduction in the amount of, particularly, the crosslinked structures formed by reaction between (B) and the carbodiimide groups of the polycarbodiimide in the resulting glove; therefore, such a condition needs to be avoided.

Meanwhile, the structures (A) represented by ((—COO$^-$)$_2$Ca$^{2+}$) in the elastomer are required for the elastomer to remain as a cured film precursor without being dissolved in the subsequent leaching step.

Therefore, for the gelling, it is preferred to set the conditions as appropriate taking into consideration the thickness and the like of the resulting glove and to, at the same time, make adjustments in such a manner to prevent the reaction yielding ((—COO$^-$)$_2$Ca$^{2+}$) from proceeding excessively while surely allowing the reaction to occur.

The ratio of (A) and (B) in the elastomer varies depending on the conditions of the gelling step.

The ratio of the above-described (A) in the elastomer mainly affects the tensile strength of the resulting glove, the inhibition of a reduction in tensile strength in an artificial sweat solution and the organic solvent impermeability, and the ratio of the above-described (B) in the elastomer mainly affects the fatigue durability in terms of ensuring the reaction with the carbodiimide groups.

Accordingly, the conditions of the gelling step may greatly affect the physical properties of the resulting glove as a desired final product.

In view of the above, the conditions of the gelling step in the method of producing a glove according to one embodiment of the present invention are required to satisfy the following points.

(i) Calcium of the coagulant and ammonium salts and/or amine salts of the carboxyl groups of the elastomer moderately react with each other to be bound. The reason for this is that, when the gelling proceeds overly, the amount of the ammonium salts of the carboxyl groups remaining in the elastomer as well as the amount of the carboxyl groups (—COOH) become excessively small, leaving an insufficient amount of carboxyl groups to be bound with the carbodiimide groups.

(ii) The gelling step should not be performed at a high temperature such that ammonium salts (—COO$^-$NH$_4^+$) and/or amine salts (—COO$^-$NHR$_3^+$, —COO$^-$NH$_2$R$_2^+$, —COO$^-$NH$_3$R$^+$) of the carboxyl groups of the elastomer contained in the glove dipping composition are not excessively substituted to ((—COO$^-$)$_2$Ca$^{2+}$) by Ca$_2^+$activated at the high temperature.

This enables to secure the ratio of (—COOH) to be crosslinked with polycarbodiimide groups in the curing step.

Further, at a high temperature, ammonium salts (—COO$^-$NH$_4^+$) make the pH adjustment difficult since the salts cause intense volatilization of NH$_3$ in particular and form NH$_4$NO$_3$.

It is noted here that, in cases where volatile ammonia is used as a pH modifier, the pH needs to be maintained in all of the steps up to this point.

(iii) Such drying that causes the hydrophilic segment of the polycarbodiimide to open should not be performed. In the method of producing a glove according to one embodiment of the present invention, the polycarbodiimide contained in the glove dipping composition has a hydrophilic segment. By the drying performed in the below-described curing step, the hydrophilic segment is opened and the carbodiimide groups are exposed, as a result of which the reaction with (—COOH) described in the above (ii) occurs, and crosslinks are thereby formed. Thus, in the gelling step, it is necessary to avoid such excessive drying that causes the hydrophilic segment of the polycarbodiimide to open.

In view of the above, the following modes can be exemplified as the conditions of the gelling step in one embodiment of the present invention.

For those cases where no humectant is incorporated into the glove dipping composition, examples of the conditions of the gelling step include a mode of leaving the glove dipping composition to stand at room temperature (15 to 25° C., more specifically about 23° C.) for 20 seconds to 20 minutes, preferably for 30 seconds to 10 minutes, and a mode of leaving the glove dipping composition to stand at 50 to 70° C. for 20 seconds to 3 minutes, or for 30 seconds to 2 minutes.

In cases where a humectant is incorporated into the glove dipping composition, as the conditions of the gelling step, the same conditions as those of the above-described cases where no humectant is incorporated can be adopted and, for example, a mode of leaving the glove dipping composition at 50 to 70° C. for less than 20 minutes may be adopted as well.

In the gelling step, the term "leaving" means that an operation of, for example, adding a certain substance to the mold or the former to which the glove dipping composition has adhered is not performed, and the term encompasses not only a state where the mold or the former is placed still, but also a state where, in an ordinary factory, the mold or the former is being moved on the production line without being placed still.

For any of the above-described conditions, basically, it is preferred to perform the "leaving" at an ambient temperature (room temperature) in the glove production, that is, not to perform heating. In the glove production, depending on the location of the factory, the ambient temperature (room temperature) can be about 23° C., or about 50° C. The above-mentioned temperature ranges take the locations of such factories into account and, even if the "leaving" is to be done at, for example, about 50° C., it is not basically expected to raise the temperature thereto by heating.

The gelling step may be performed, for example, under a condition of 40% to 60% RH (relative humidity).

(e) Leaching Step

The leaching step is the step of, after the above-described gelling step, washing the mold or the former, to which the elastomer has adhered, with water and thereby removing chemical agents. In this step, the mold or the former which is coated with the elastomer that has been partially dried is washed with water (leached) in hot water or warm water (30 to 80° C.) for 30 seconds to 15 minutes, preferably for 4 to 6 minutes or so.

By performing the leaching, components derived from the coagulant, such as calcium ions and nitrate ions, as well as components derived from the pH modifier, such as ammonium ions, are removed. As a result, excessive gelling can be inhibited.

Further, in this leaching step, the structures of zinc hydroxide complexes and aluminum complexes are broken and these complexes are converted into the forms of Zn$^{2+}$ and Al$^{3+}$, allowing them to form ionic bonds with the carboxyl groups of the elastomer. It is believed that, as described above, these ionic bonds are formed from some of the structures (A) and some of the salts (—COO$^-$NH$_4^+$) of the structures (B) in the later steps of (g) and (h).

(f) Beading Step

The beading step is the step of, after the completion of the leaching step, performing a sleeve winding process in the cuff part of the resulting glove.

(g) Precuring Step

Subsequently, the mold or the former is dried in a furnace at 60 to 90° C., more preferably 65 to 80° C., for 30 seconds to 10 minutes (precuring step).

By incorporating this step, partial expansion of the resulting glove that may occur due to rapid reduction in water content in the subsequent step (h) can be inhibited.

(h) Curing Step

The curing step is the step of heating the mold or the former, which has been dried in the above-described step (g), at such a temperature for such a period that are sufficient for the ammonium salts of the elastomer to be converted back to carboxyl groups by a high temperature, the carbodiimide groups of the polycarbodiimide to be exposed, and the carboxyl groups of the elastomer and the carbodiimide groups of the polycarbodiimide to react with each other.

More specifically, the curing step is the step of crosslinking and curing the elastomer by, for example, heating at 70 to 140° C. for 10 to 30 minutes.

In this step (h), the elastomer is crosslinked by the polycarbodiimide and molecular chains are thereby formed, so that a variety of preferred properties can be imparted to the resulting glove. In other words, although the carboxyl groups of the elastomer form ammonium salts (—COO$^-$NH$_4^+$) and/or amine salts in water and are thus in an equilibrium state with (—COOH), it is believed that these salts are converted back to carboxyl groups (—COOH) as dehydration proceeds by drying, as a result of which these carboxyl groups, along with (—COOH) of (B), react with the carbodiimide groups.

Further, the formation of ionic bonds by reaction between some of the calcium salts ((—COO$^-$)$_2$Ca$^{2+}$) and ammonium salts (—COO$^-$NH$_4^+$) of the carboxyl groups and the zinc ions and/or aluminum ions is completed in this step (h).

Therefore, the number ratio of the crosslinked structures formed by reaction between the carboxyl groups and the carbodiimide groups, the crosslinked structures formed by reaction between the carboxyl groups and the calcium ions, and the crosslinked structures formed by reaction between the carboxyl groups and the zinc ions and/or aluminum ions is established in this step (h).

In the present invention, the curing (crosslink-curing) can also be performed at, for example, 70 to 80° C., which is conventionally considered as a low-temperature condition. This is advantageous in terms of the production cost since conventional sulfur crosslinking requires a crosslinking temperature of about 120° C.

In the above-described production process, the glove forming mold is immersed in the composition for dip-molded article only once; however, in the present invention, a glove can also be produced by performing the immersion operation plural times (a maximum of about three times). Such a method is effective for inhibiting the generation of pinholes, which is a concern when a thin glove of about 50 µm in thickness is to be produced. This method is also an effective means for producing a thick glove.

When the immersion operation is performed plural times, the gelling step is incorporated after each immersion operation, and the subsequent immersion operation is performed after the formation of a certain amount of Ca crosslinks.

According to the studies conducted by the present inventors, as described above, when the pH modifier is an ammonium compound or an amine compound, the ammonium component or the amine component can be released from carboxylate by heating to yield a carboxyl group; however, when the pH modifier is commonly-used potassium hydroxide, since it remains to stably exist as a carboxylate (—COO—K$^+$) and is not converted back to a carboxyl group, there is a problem that the reaction with the carbodiimide groups is inhibited.

According to the studies conductive by the present inventors, when all of the carboxyl groups in the elastomer are crosslinked by calcium alone and the elastomer is XNBR NL120H (carboxylic acid content: 5.3% by weight), about 80% of the carboxyl groups are consumed, leaving about 20% of the carboxyl groups. Further, when a carbodiimide (E-02) was added thereto in a range of from 1 to 10% by weight, the reduction in the amount of residual carboxyl groups was very small when the carbodiimide was added in an amount of up to 3% by weight; however, the amount of residual carboxyl groups was 0 when the carbodiimide was added in an amount of 7% by weight.

As compared to the calcium content in a cured film obtained by crosslinking the elastomer with calcium alone, the calcium content in a cured film obtained with an addition of 3% by weight of the polycarbodiimide was only slightly reduced; therefore, it is presumed that the polycarbodiimide has a maximum capacity of crosslinking about 20% of the carboxyl groups contained in the elastomer and that, in the use of the polycarbodiimide in an ordinary amount of 3% by weight or less, the polycarbodiimide reacts with several % of the carboxyl groups contained in the elastomer. As a result, high fatigue durability is provided.

Meanwhile, since carbodiimide groups have substantially no contribution to the tensile strength, in the present invention, the tensile strength is provided by crosslinks formed by calcium, zinc and/or aluminum.

Further, inhibition of a reduction in tensile strength in an artificial sweat solution as well as the organic solvent impermeability are achieved by crosslinks formed by zinc and/or aluminum.

In this manner, in the present invention, the shortcomings of the respective crosslinking agents are improved and a glove comparable to a conventional sulfur-based XNBR glove is produced by using a combination of the crosslinking agents each in the smallest amount possible.

3. Glove According to One Embodiment of the Present Invention

The glove according to one embodiment of the present invention can be produced in accordance with the above-described method of producing a glove according to one embodiment of the present invention using the above-described glove dipping composition according to one embodiment of the present invention.

The glove according to one embodiment of the present embodiment is composed of a cured film formed by curing, for example, the above-described glove dipping composition, and the elastomer (XNBR) contained in the cured film may have, for example, the same formulation as the glove dipping composition. Further, the cured film has crosslinks formed by a polycarbodiimide (CDI crosslinks), crosslinks formed by calcium (Ca crosslinks), and crosslinks formed by zinc oxide (Zn crosslinks) and/or crosslinks formed by an aluminum complex (Al crosslinks).

The glove according to one embodiment of the present embodiment is believed to have the crosslinked structures illustrated in FIG. 1.

The elastomer (XNBR) according to this embodiment of the present invention is bound by crosslinks between carboxyl groups originating from an unsaturated carboxylic acid polymerized in the main chain. The crosslinks between the carboxyl groups are generally classified into two types, which are crosslinks formed by the polycarbodiimide and crosslinks formed by polyvalent metal ions, and the polyvalent metal ions always include Ca$^{2+}$ originating from a coagulant and further include Zn$^{2+}$ and/or Al$^{3+}$. The crosslinking by the polycarbodiimide is characterized by having a relatively long distance between crosslinking points and thus being capable of crosslinking the elastomer (XNBR) molecules that are not adjacent to each other as well as being capable of forming crosslinks at multiple points, and it is believed that such loose integration of the elastomer (XNBR) by a large structure greatly contributes to the fatigue durability. Further, the crosslinks formed by the polycarbodiimide are not easily broken since they are covalent bonds. Meanwhile, the crosslinking by the polyvalent metal ions is characterized by having a relatively short distance between crosslinking points and is believed to contribute to the tensile strength by crosslinking and fixing adjacent XNBR molecules and thereby forming strong crosslinked structures. In addition, the crosslinks formed by the polyvalent metal ions also have a function of reducing the organic solvent impermeability. However, they are ionic bonds and are thus easily broken due to elution of the ions caused by salts and acids that are contained in sweat. Particularly, elution of $Ca^{2+}$ is likely to occur and, therefore, as in the glove according to one embodiment of the present embodiment, Zn crosslinks and/or Al crosslinks that are unlikely to cause elution are indispensable.

When aluminum is not incorporated, the content of elemental zinc in the glove according to one embodiment of the present invention is, for example, roughly 0.05 to 2.5% by weight, preferably 0.05 to 2.3% by weight, more preferably 0.15 to 2.0% by weight, with respect to the total amount of the glove. When zinc is not incorporated, the content of elemental aluminum is, for example, roughly 0.05 to 0.8% by weight or 0.05 to 0.7% by weight, preferably 0.1 to 0.6% by weight.

When the glove according to one embodiment of the present invention contains both zinc and aluminum, the total content of these elements is, for example, 0.05 to 3.3% by weight, or 0.2 to 1.5% by weight.

The glove according to one embodiment of the present invention usually contains calcium in an amount of 0.1 to 2.3% by weight and may take, for example, a mode of containing 0.2 to 2.0% by weight of calcium, or a mode of containing 0.5 to 1.5% by weight of calcium.

The glove according to one embodiment of the present invention has sufficient mechanical properties (strength and rigidity) also as a thin glove. The thickness of the glove is not particularly restricted; however, it is preferably 0.04 to 0.35 mm, more preferably 0.04 to 0.3 mm.

When the glove according to the present embodiment is used as a thin glove, the thickness thereof is preferably 0.04 to 0.15 mm, while when the glove is used as a thick glove, the thickness thereof is preferably greater than 0.15 mm to 0.4 mm.

The glove according to one embodiment of the present invention has the following performances of (1) and (2):
(1) a fatigue durability of 200 minutes or longer; and
(2) a tensile strength of 20 MPa or higher.

In the glove according to one embodiment of the present invention, as compared to a glove composed of crosslinks formed by a polycarbodiimide alone, a marked reduction in the tensile strength in an artificial sweat solution is inhibited and the organic solvent impermeability is improved.

A glove having such performances that are comparable to or superior to those of a conventional sulfur-based XNBR glove can be obtained using the respective crosslinking agents in small amounts.

According to the studies conducted by the present inventors, conventional XNBR gloves exhibit a fatigue durability of about 200 to 400 minutes in a fatigue durability test (test method is described below); however, according to the production method of the present embodiment, gloves that are not torn even after 25 hours in a fatigue durability test can be provided depending on the amounts of the respective components. Further, by adjusting the amount of zinc oxide and/or aluminum complex to be added, the tensile strength and the inhibition of reduction in the tensile strength in an artificial sweat solution as well as the organic solvent impermeability can be adjusted in a variety of manners.

Moreover, a variety of gloves can be produced, ranging from ordinary gloves (3.7 g, thickness: about 70 μm) and ultra-thin gloves (3.0 g, thickness: about 50 μm) to thick groves for cooking (thickness: 150 to 300 μm).

4. Problem-Solving in the Present Invention (1) In those gloves obtained by molding a glove dipping composition containing a polycarbodiimide as a crosslinking agent, Ca crosslinks attributed to a coagulant plays an important role by contributing to the initial tensile strength; however, with only the crosslinks formed by the polycarbodiimide and Ca crosslinks, there are drawbacks in terms of reduction in tensile strength in an artificial sweat solution and the organic solvent impermeability. On the other hand, in the glove according to one embodiment of the present invention, such drawbacks are overcome by a combination of CDI crosslinks, Zn crosslinks and/or Al crosslinks. As specific effects thereof, a reduction in tensile strength in an artificial sweat solution was inhibited, and the organic solvent impermeability was improved (e.g., the below-described Experiments (3), (8) and (10)).

(2) By using the above-described crosslinking agents in combination, the problem of producing a glove that has performances equivalent to those of an XNBR grove containing conventionally standard sulfur as a crosslinking agent with the use of the respective crosslinking agents in the smallest amount possible was resolved by the below-described Experiment (5) and the like.

In the present invention, even an unprecedentedly thin glove (thickness: about 55 μm) having sufficient performances as a glove can be obtained by, for example, using only a small amount of a polycarbodiimide at 0.5% by weight and a small amount of zinc oxide at 1% by weight in a glove dipping composition and adopting such rigorous gelling conditions of 55° C. for 130 seconds and an unprecedentedly low curing temperature of 70° C. (below-described Experiment (13)).

EXAMPLES

In the following (1) to (4), the results of experiments that were conducted to examine the various conditions according to the embodiments of the present invention are described. It is noted here that, hereinafter, an elastomer having crosslinks formed by the elastomer itself may be abbreviated as "self-crosslinked" elastomer, and a crosslink formed via a polycarbodiimide, a crosslink formed via a calcium ion, a crosslink formed via a zinc ion, a crosslink formed via an aluminum ion and a crosslink formed via sulfur may be abbreviated as "CDI crosslink" "Ca crosslink", "Zn crosslink", "Al crosslink" and "S crosslink", respectively.

(1) Examination of Polycarbodiimides

As polycarbodiimides, CARBODILITE E-05, V-02-L2, V-04, E-03A, E-02 and V-02 (trade names, manufactured by Nisshinbo Holdings Inc.) were used. Table 1 shows the information of the respective polycarbodiimides. In accordance with the below-described <Production of Glove Dipping Solutions>, <Preparation of Coagulants> and <Production of Cured Films>, dipping compositions and test films were prepared using the respective polycarbodiimides shown in Table 1 along with NL120H manufactured by LG Chem Ltd. as an elastomer. For each of the thus obtained films, the tensile strength was measured in accordance with the test method described below in the section of (Fatigue Durability) under <Evaluation of Cured Films>.

TABLE 1

| Polycarbodiimide as Crosslinking Agent | | | | | | | |
|---|---|---|---|---|---|---|---|
| | | Type of polycarbodiimide | | | | | |
| | | E-05 | V-02-L2 | V-04 | E-03A | E-02 | V-02 |
| Structure of hydrophilic segment[Note 1] | | PEGME | PEGME | PEGME | PEGME | PEGME | PEGME |
| Structure of polycarbodiimide crosslinking agent[Note 2] (Type of organic diisocyanate) | | DCHM | DCHM | TMX | DCHM | DCHM | DCHM |
| Number-average molecular weight (measured value) | | 1,200 | 3,600 | 1,900 | 3,400 | 1,800 | 2,500 |
| Average polymerization degree = Number-average molecular weight/Equivalent (calculated value) | | 3.9 | 9.4 | 5.7 | 9.3 | 4 | 4.2 |
| Equivalent = Molecular weight/Polymerization degree (catalog value; Nisshinbo Chemical Inc.) | | 310 | 385 | 335 | 365 | 445 | 590 |
| Fatigue durability (min)[Note 3] | Polycarbodiimide 1% by weight | >1,500 | >1,500 | >1,500 | >1,500 | 76 | 29 |
| | Polycarbodiimide 3% by weight | >1,500 | >1,500 | >1,500 | >1,500 | >1,500 | >1,500 |

[Note 1] PEGME: polyetylene glycol monometyl ether
[Note 2] DCHM: dicyclohexylmethane-4,4'-diisocyanate, TMX: m-tetramethylxylylene diisocyanate
[Note 3] Measured for a film (thickness: 70 μm) formed on a ceramic plate. Gelling conditions: at 50° C. for 20 minutes, no humectant According to the results shown in Table 1, good fatigue durability was attained in all of the cases where one of the above-described polycarbodiimides having a hydrophilic segment was used. Particularly, in those cases where E-05, V-02-L2, V-04 or E-03A was used, extremely good fatigue durability was attained even when the polycarbodiimide was added to each dipping composition in an amount of 1% by weight. When each polycarbodiimide was added in an amount of 3% by weight, a fatigue durability of longer than 1,500 minutes was attained in a carbodiimide equivalent range of 260 to 600, as long as the polycarbodiimide had a hydrophilic segment.

However, when each polycarbodiimide was added in an amount of 1% by weight, the fatigue durability was extremely low (100 minutes or shorter) at an equivalent value of higher than 440. Accordingly, the carbodiimide equivalent is preferably in a range of 260 to 440. It is noted here that the lower limit of the equivalent of 260 is that of a range that yields a product.

(2) Comparison of Physical Properties (Swelling in Artificial Sweat Solution and Reduction in Tensile Strength after Immersion in Artificial Sweat Solution) Between Gloves Crosslinked by Polycarbodiimide in Dipping Composition (Containing Neither Zinc Oxide Nor Aluminum Complex) and Commercially Available Gloves Using the elastomer shown in Table 2, a glove dipping composition containing a polycarbodiimide (E-02) as a crosslinking agent was prepared, and a glove of Comparative Example 1 was produced in accordance with the glove production steps shown in FIGS. 6-1 and 6-2. In addition, the three kinds of commercially available gloves shown in Table 2 (SF-7000, VERTE-710 and SafeTouch) were prepared. The crosslinking modes of these gloves were as follows.

Comparative Example 1: CDI-crosslinked glove (CDI crosslinking+Ca crosslinking)

Reference Example 1: self-crosslinked glove, product name: CheMax SF7000 (self-crosslinking+Zn crosslinking+Ca crosslinking)

Reference Example 2: S-crosslinked glove, product name: VERTE 710 (S crosslinking+Zn crosslinking+Ca crosslinking)

Reference Example 3: Al-crosslinked glove, product name: SafeTouch (Al crosslinking+Ca crosslinking)

The above-described gloves were each subjected to an immersion test. As for the immersion conditions, each glove was immersed for 20 hours in three conditions of 50° C. water, 23° C. artificial sweat solution and 50° C. artificial sweat solution. The tensile strength, the elongation and the contents of Ca, Zn and Al in each glove were measured before and after the immersion, and the thus measured values were compared and examined.

The results thereof are shown in Table 2 and FIG. 2. Referring to the results shown in Table 2 and FIG. 2, it was found that all of the gloves substantially maintained the tensile strength and the elongation in water (50° C.); however, in the artificial sweat solutions, particularly in the artificial sweat solution at 50° C., the performances of the gloves were deteriorated with the tensile strength retention rate being the lowest and the elongation being the highest accordingly. In addition, it was found that Reference Example 2 (S-crosslinked glove) showed less deterioration in the performances than the non-S-crosslinked gloves (Comparative Example 1 and Reference Examples 1 and 3). Thereamong, Comparative Example 1 (CDI-crosslinked glove) was found to have the largest deterioration.

In the CDI-crosslinked glove of Comparative Example 1, the tensile strength was maintained by the bonds formed by $Ca^{2+}$ contained in the coagulant; therefore, it was assumed that Ca crosslinks caused the reduction in tensile strength in the artificial sweat solutions.

Accordingly, for Ca, Zn and Al contributing to the crosslinked structures of the respective crosslinked gloves, the content in each glove was measured before and after the immersion in the artificial sweat solutions (see Table 2).

Examining the results of measuring the metal contents shown in Table 2, it is seen that, with regard to Ca crosslinks common to all of the gloves, Ca eluted into the artificial sweat solutions. Further, it was found that, although Zn eluted from the gloves having Zn crosslinks, hardly any Al eluted from the glove having Al crosslinks. Meanwhile, comparing the gloves, it was found that the gloves of Reference Examples 1 and 2 having Zn crosslinks exhibited a relatively high tensile strength retention rate.

From the above, it was conceived to solve the problems by using Zn and/or an Al complex in combination in a CDI-crosslinked glove.

Glove Dipping Solutions>, <Preparation of Coagulants> and <Production of Cured Films>, and test films were prepared.

TABLE 2

Comparison of Glove Crosslinked by Polycarbodiimide(Note 1) and Commercially Available Gloves

|  |  |  |  | Comparative Example 1 | Reference Example 1 | Reference Example 2 | Reference Example 3 |
|---|---|---|---|---|---|---|---|
|  | Sample(Note 1) |  |  | CDI-only crosslinked glove | SF-7000 | VERTE-710 | SafeTouch |
| XNBR |  | Type |  | NL120H | 746SXL (self-linking) | X6311 | not clear |
|  |  | Mooney viscosity ($ML_{(1+4)}$ 100° C.) |  | 111 | 156 | 95 | — |
|  |  | MEK-insoluble conent (% by weight) |  | 5.6 | 64 | 60 | — |
|  |  | Amount of MMA (COOH) (% by weight) |  | 5.3 | 2.9 | 3.1 | — |
|  |  | Amount of AN (% by weight) |  | 28 | 28 | 26 | — |
| (Note 2) Crosslinking agent |  | $Ca^{2+}$ (coagulant) (○: present, X: absent) |  | ○ | ○ | ○ | ○ |
|  | Polycarbodiimide | Type |  | E-02 | — | — | — |
|  |  | Added amount (% by weight) |  | 3 | — | — | — |
|  | Amount of added ZnO (% by weight) |  |  | — | ○ | ○ | — |
|  | Al complex | Type |  | — | — | — | not clear |
|  |  | Added amount (% by weight) |  | — | — | — | ○ |
| Physical properties |  | Tensile strength (MPa) (target value ≥ 20 MPa) |  | 23 | 30 | 35 | 20 |
|  |  | Elongation (%) |  | 636 | 591 | 534 | 635 |
|  | Inhibition of reduction in physical properties in artificial sweat solution | Tensile strength (MPa) after 20-hour immersion | Water, at 50° C. | 26 (113) | 26 (87) | 28 (80) | 20 (100) |
|  |  | Retention rate (%) in parentheses | Artificial sweat solution, at 23° C. | 11 (48) | 16 (53) | 24 (69) | 8 (40) |
|  |  |  | Artificial sweat solution, at 50° C. | 6 (26) | 11 (37) | 18 (51) | 7 (35) |
|  |  | Elongation (%) after 20-hour immersion | Water, at 50° C. | 650 (102) | 606 (103) | 543 (102) | 658 (104) |
|  |  | Rate of increase (%) in parentheses | Artficial sweat solution, at 23° C. | 788 (124) | 700 (118) | 611 (114) | 574 (90) |
|  |  |  | Artficial sweat solution, at 50° C. | 1,000 (157) | 764 (129) | 646 (121) | 604 (95) |
|  |  | Organic solvent impermeability(Note 3) |  | X | ○ | ○ | ◎ |
| (Note 4)Metal content | Ca (% by weight) | before immersion |  | 1.04 | 0.74 | 0.7 | 1.05 |
|  |  | Water, at 50° C. |  | 1.03 | 0.7 | 0.65 | 0.83 |
|  |  | Artificial sweat solution, at 23° C. |  | 0.86 | 0.62 | 0.66 | 0.41 |
|  |  | Artificial sweat solution, at 50° C. |  | 0.68 | 0.48 | 0.57 | 0.11 |
|  | Zn (% by weight) | before immersion |  | ND | 0.88 | 1.1 | ND |
|  |  | Water, at 50° C. |  | ND | 0.88 | 1.1 | ND |
|  |  | Artificial sweat solution, at 23° C. |  | ND | 0.74 | 1.04 | ND |
|  |  | Artificial sweat solution, at 50° C. |  | ND | 0.51 | 0.83 | ND |
|  | Al (% by weight) | before immersion |  | ND | ND | ND | 0.38 |
|  |  | Water, at 50° C. |  | ND | ND | ND | 0.38 |
|  |  | Artificial sweat solution, at 23° C. |  | ND | ND | ND | 0.37 |
|  |  | Artificial sweat solution, at 50° C. |  | ND | ND | ND | 0.37 |

(Note 1)Sample: Comparative Example 1 was a glove produced by polycarbodiimide crosslinking (thickness: 70 μm), Gelling conditions: at 50° C. for 20 minutes Reference Examples 1 to 3 were commercially available gloves.
(Note 2) Crosslinking agents: ZnO, Al complex; ○ indicating addition in an unknown amount
(Note 3)Organic solvent impermeability: particularly good = ◎, good = ○, poor = X
(Note 4)Metal content ND = less than detection limit (0.05% by weight)

(3) Measurement of Organic Solvent Impermeability (Comparison and Examination of Crosslinking Agents in Measurement of Organic Solvent Impermeability)

A glove according to the present invention (Example 1: a film obtained from a dipping composition containing an XNBR, zinc oxide and a polycarbodiimide) was subjected to an organic solvent impermeability test. In addition, for comparison, the test was also carried out for a case where crosslinking was performed by the polycarbodiimide alone (Comparative Example 2), cases where crosslinking was performed by self-crosslinking and zinc oxide (Reference Examples 4 and 5), a case where crosslinking was performed by sulfur and zinc oxide (Reference Example 6), and a case where crosslinking was performed by an epoxy compound and aluminum (Reference Example 7).

For the film of Example 1, the dipping composition and a test film were prepared in the same manner as in the above (1) in accordance with the below-described <Production of The organic solvent impermeability was evaluated in terms of swelling by two methods using the Hansen solubility parameters (HSP). For the organic solvent impermeability, the glove of the present invention (crosslinked by calcium, zinc oxide and/or an aluminum complex, and a polycarbodiimide) was compared and examined against XNBR gloves that were obtained by crosslinking performed by a polycarbodiimide alone, a combination of self-crosslinking and Zn crosslinking, a combination of sulfur crosslinking and Zn crosslinking, or crosslinking performed by Al alone. The organic solvent impermeability was evaluated based on the swelling against organic solvents that was measured by the following two methods of (a) and (b) using the Hansen solubility parameters (HSP). The details thereof are described below.

(a) Evaluation Based on Radius (R) of Interaction Sphere

Table 3 shows the results of evaluating the radius (R) of the interaction sphere derived from the Hansen solubility parameters (HSP). An interaction sphere is a sphere that encapsulates good solvents (solvents likely to cause swelling, set for about 10 kinds) when the HSP distance is measured for 24 kinds of solvents and the measured values are resolved into the dispersion term (dD), the polar term (dP) and the hydrogen bond term (dH) and then plotted in a three-dimension. A smaller radius (R) indicates that the subject glove is less likely to be swollen (i.e., superior organic solvent impermeability).

The following solvents were used: n-hexane, cyclohexane, methyl isobutyl ketone, n-butyl acetate, toluene, tetrahydrofuran (THF), methyl ethyl ketone (MEK), chloroform, methyl acetate, acetone, 1,4-dioxane, pyridine, N-methylpyrrolidone, hexafluoroisopropanol, 1-butanol, acetonitrile, diethylene glycol, N,N-dimethylformamide, γ-butyrolactone, ethanol, dimethyl sulfoxide, methanol, 2-aminoethanol, and cyclohexanone.

It was found that, although the glove of Comparative Example 2 containing only crosslinks formed by the polycarbodiimide had the largest value of R among the six tested gloves and thus would be likely to be swollen, the glove of Example 1 in which crosslinks formed by zinc oxide were added had a smaller value of R than the sulfur-free gloves SF-7000 (Reference Example 4) and HGC-100 (Reference Example 5) and its organic solvent impermeability was at the level usually required for a nitrile glove.

Figure 5:
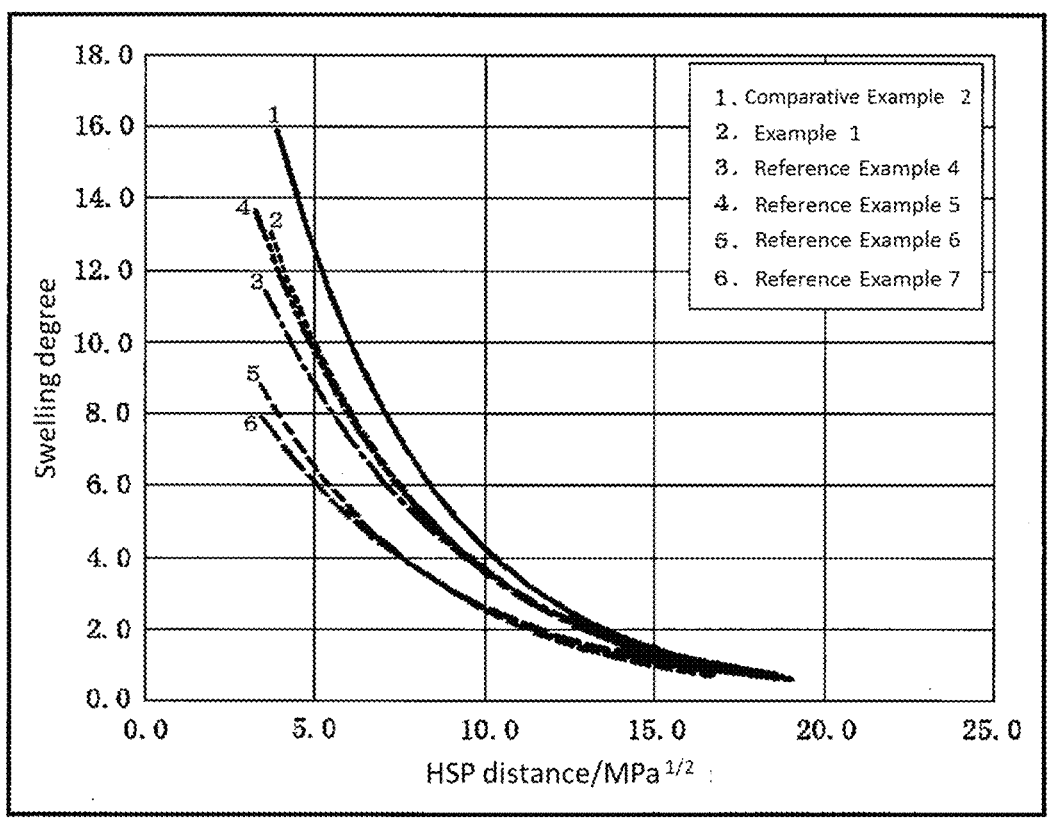
FIG. 5 is a graph showing the results of a test performed on various gloves for verification of the organic solvent impermeability. The swelling degree and the HSP distance determined by using 24 kinds of organic solvents are plotted on the ordinate and the abscissa, respectively, and the organic solvent impermeability is judged based on the slope of each curve.

(b) Evaluation Based on Slope of Correlation Curve of Swelling Degree and HSP Distance Taking advantage that the HSP distance derived from the Hansen solubility parameters has a negative correlation with the swelling degree, FIG. 5 was prepared from the measurement results of the 24 kinds of organic solvents for each sample by plotting the HSP distance on the abscissa and the swelling degree on the ordinate, and the swelling of each sample was evaluated based on the slope of an approximate curve (correlation curve). It can be judged that the smaller the slope, the less likely that the sample will be swollen. The results were substantially the same as those of the evaluation based on R. Comparative Example 2 had the largest slope; however, an addition of Zn crosslinks thereto (Example 1) allowed the glove to have organic solvent impermeability comparable to those of the Zn-crosslinked+self-crosslinked gloves (Reference Examples 4 and 5). However, the organic solvent impermeability of the glove of Example 1 did not reach the level of the S-crosslinked+Zn-crosslinked glove (Reference Example 6) or the Al-crosslinked glove (Reference Example 7).

In a case where a CDI-crosslinked (multipoint-crosslinked) glove is imparted with fatigue durability by crosslinks formed by a polycarbodiimide and the crosslinks are densified by Ca crosslinking and the glove contains both polycarbodiimide crosslinks and Ca crosslinks, the Ca crosslinks are responsible for the organic solvent impermeability of the CDI-crosslinked (multipoint-crosslinked) glove.

However, since Ca crosslinks have a large ionic bond radius than Zn crosslinks, it is believed that such a glove has low organic solvent impermeability and is thus swollen.

This is one of the factors for arriving at the present invention in which some of the Ca crosslinks are substituted with Zn crosslinks or Al crosslinks having even higher bonding strength

TABLE 3

Evaluation of Swelling against Organic Solvents based on Radius (R) of Interaction Sphere

| | | | Example 1 | Comparative Example 2 | Reference Example 4 | Reference Example 5 | Reference Example 6 | Reference Example 7 |
|---|---|---|---|---|---|---|---|---|
| | Sample[Note 1] | | CDI + metal-crosslinked film | CDI-crosslinked film | SF-7000 (for food products) | HGC-100 (for clean room) | VERTE710N | Top Glove |
| XNBR | Type | | NL120H | NL120H | 746SXL (self-crosslinking) | 746SXL (self-crosslinking) | X6311 | not clear |
| | Mooney viscosity (ML$_{(1+4)}$ 100° C.) | | 111 | 111 | 156 | 156 | 95 | not clear |
| | MEK-insoluble content (% by weight) | | 5.6 | 5.6 | 64 | 64 | 60 | not clear |
| | Amount of MMA (COOH) (% by weight) | | 5.3 | 5.3 | 2.9 | 2.9 | 3.1 | not clear |
| | Amount of AN (% by weight) | | 28 | 28 | 28 | 28 | 26 | not clear |
| | Butadene (% by weight) | | 66.7 | 66.7 | 69.1 | 69.1 | 70.9 | not clear |
| [Note 2]Cross-linking agent | Polycarbodiimide | Type | E-03A | E-03A | — | — | — | — |
| | | Added amount (% by weight) | 0.5 | 0.5 | — | — | — | — |
| | Divalent epoxy crosslinking agent (% by weight) | | — | — | — | — | — | ○ |
| | Amount of added sulfur (% by weight) | | — | — | — | — | ○ | — |
| | Amount of added ZnO (% by weight) | | 0.5 | — | ○ | ○ | ○ | — |
| | Amount of Al complex (% by weight) | | — | — | — | — | — | ○ |
| Evaluation of swelling | HSP distance (Ma$^{1/2}$) | Dispersion term, dD | 19.90 | 20.52 | 20.21 | 20.06 | 19.37 | 19.59 |
| | | Polar term, dP | 6.38 | 7.59 | 7.70 | 6.95 | 7.95 | 7.05 |
| | | Hydrogen bond term, dH | 8.01 | 7.98 | 7.74 | 8.05 | 9.10 | 8.56 |
| | | Total | 22.46 | 23.29 | 22.97 | 22.70 | 22.83 | 22.51 |
| | Radius of Interaction sphere, R | | 8.7 | 9.9 | 9.6 | 9.1 | 7.9 | 8.2 |

[Note 1]Sample: a film (thickness: 70 μm) formed on a ceramic plate for Example 1 and Comparative Example 2, Gelling conditions: at 23° C. for 1 minute, no humectant; a commercially available glove for Reference Examples 4 to 7.
[Note 2]Crosslinking agent: "—" = not added, "○" = added in an unknown amount (4) Amount of Eluted Metals (Calcium and Zinc) Before and after Fatigue Durability Test As shown in Table 4, dipping compositions containing the respective polycarbodiimide and zinc oxide (Examples 2 to 5), a polycarbodiimide-free dipping composition (Comparative Example 3), zinc oxide-free dipping composition (Comparative Example 4) were prepared, and test films were produced in the same manner as in the above-described (1).

For the thus obtained films, the contents of metals (calcium and zinc) were measured before and after a fatigue durability test (immersion in an artificial sweat solution), and the amounts of eluted metals were determined.

Based on Table 4 showing the results obtained for Examples 2 to 5 where 1% by weight of a polycarbodiimide and 0.5% by weight of zinc oxide were incorporated, Comparative Example 3 where only zinc oxide was incorporated in an amount of 3% by weight and Comparative Example 4 where only a polycarbodiimide was incorporated in an amount of 3% by weight, calcium was more easily eluted than zinc.

With regard to these products, Table 1 shows the structure, the number-average molecular weight, the average polymerization degree and the equivalent.

<Zinc Oxide>

As zinc oxide (ZnO), a 50% zinc oxide solution (aqueous zinc white AZ-SW, manufactured by Osaki Industry Co., Ltd.) was used. Zinc oxide forms a hydroxyl group-coordinated anionic complex in a glove dipping composition.

<Aluminum Complexes>

Aluminum complexes were prepared as follows.

(A) Aluminum Hydroxide Complex

After dissolving 0.45 g of $AlCl_3 \cdot 6H_2O$ in 20 mL of water, the resulting solution was stirred and 7 to 7.5 mL of a 7% aqueous $NaHCO_3$ solution was slowly added thereto. Although $NaHCO_3$ was added in an amount slightly greater than the aluminum equivalent, the resultant had a pH of 6.5 to 7.0. The pH was adjusted to be 9 to 9.5 by adding thereto 0.5 to 1.0 mL of 8% NaOH. The thus prepared gel-form complex maintained a dispersed state with no precipitation for at least one night even without stirring.

TABLE 4

Elution of Ca and Zn caused by fatigue durability test (immersion in artificial sweat solution)

| | | | Example 2 | Example 3 | Example 4 | Example 5 | Comparative Example 3 | Comparative Example 4 |
|---|---|---|---|---|---|---|---|---|
| X-NBR | Type | | NL120H | NL120H | NL120H | NL120H | NL120H | NL120H |
| | Mooney viscosity ($ML_{(1+4)}$ 100° C.) | | 111 | 111 | 111 | 111 | 111 | 111 |
| | MEK-insoluble content (% by weight) | | 5.6 | 5.6 | 5.6 | 5.6 | 5.6 | 5.6 |
| | Amount of MMA (COOH) (% by weight) | | 5.3 | 5.3 | 5.3 | 5.3 | 5.3 | 5.3 |
| | Amount of AN (% by weight) | | 28 | 28 | 28 | 28 | 28 | 28 |
| | Butadiene (% by weight) | | 66.7 | 66.7 | 66.7 | 66.7 | 66.7 | 66.7 |
| Crosslinking agent | Polycarbodiimide | Type | E-02 | E-03A | E-05 | V-02-L2 | — | E-02 |
| | | Added amount (% by weight) | 1 | 1 | 1 | 1 | — | 3 |
| | Amount of added ZnO (% by weight) | | 0.5 | 0.5 | 0.5 | 0.5 | 3 | — |
| pH | Adjusted value | | 10.5 | 10.5 | 10.5 | 10.5 | 10.5 | 10.5 |
| | Modifier | | $NH_3$ | $NH_3$ | $NH_3$ | $NH_3$ | $NH_3$ | $NH_3$ |
| | Gelling | | 50° C., 20 min | 50° C., 20 min | 50° C., 20 min | 50° C., 20 min | 23° C., 1 min | 23° C., 1 min |
| Metal content in film (% by weight) | Before fatigue durability test | Ca | 1.25 | 1.36 | 1.58 | 1.20 | 0.75 | 1.13 |
| | | Zn | 0.38 | 0.38 | 0.35 | 0.37 | 2.15 | — |
| | After fatigue durability test | Ca | 0.96 | 0.99 | 1 | 1.02 | 0.58 | 0.87 |
| | | Zn | 0.36 | 0.37 | 0.34 | 0.35 | 2.1 | — |
| Amount of eluted metal (% by weight) | | Ca | 0.29 | 0.37 | 0.58 | 0.18 | 0.17 | 0.26 |
| | | Zn | 0.02 | 0.01 | 0.01 | 0.02 | 0.05 | — |

Sample: a film formed on a ceramic plate (thickness: 70 μm), no humectant

Based on the above-described Experimental Examples of (1) to (4), experiments of Examples described below in detail were further performed.

First, the components used in Examples are each described.

<Elastomers (XNBRs)>

As XNBRs, commercially available XNBR latex products: NL105, NL107, NL111, NL12OH and NL128 (all of which are manufactured by LG Chem, Ltd., South Korea); 746SXL, X6311, 6338 and XVT-LA (manufactured by Synthomer Co., Ltd.); NBL201B (manufactured by JSR Corporation); KNL860 (manufactured by Kumho Tire Co., Ltd., Taiwan); LX550 (manufactured by ZEON Corporation); and 203A (manufactured by JSR Corporation) were used.

With regard to these products, Tables 5 to 8 and 10 to 13 below show the Mooney viscosity, the MEK-insoluble content, the methacrylic acid amount, the acrylonitrile amount and the butadiene amount.

<Polycarbodiimides>

As polycarbodiimides, CARBODILITE E-05, V-02-L2, V-04, E-03A, E-02 and V-02 (trade names, manufactured by Nisshinbo Holdings Inc.) were used.

(B) Organic Acid Complex (a) Aluminum Citrate Complex

An aluminum hydroxide gel having a pH of 6.5 to 7.0 was prepared in the same manner as described above, except that water was used in an amount of 18 mL. To the thus obtained aluminum hydroxide gel, 1/1 to 1/3 aluminum equivalent of aqueous citric acid solution (2 mL) was slowly added and, after stirring the resultant at room temperature for at least 30 minutes, the resultant was heated to 60° C., maintained for 30 minutes and then cooled, and the pH was subsequently adjusted to be 9 to 9.5 with an 8% aqueous NaOH solution. The 8% NaOH was used in an amount of about 0.5 mL (1/2 to 1/3 equivalent) to 1 mL (equivalent).

As for the outer appearance of the resulting aluminum citrate complex solution, the solution was in the form of a transparent liquid when citric acid was used at 1/1 equivalent, while the solution was turbid when citric acid was used at 1/3 equivalent.

(b) Aluminum Malate Complex

An aluminum hydroxide gel having a pH of 6.5 to 7.0 was prepared in the same manner as described above, except that water was used in an amount of 18 mL. To the thus obtained aluminum hydroxide gel, 1/1 to 1/2 aluminum equivalent of aqueous malic acid solution (2 mL) was slowly added and, after stirring the resultant at room temperature for at least 30 minutes, the resultant was heated to 60° C., maintained for 30 minutes and then cooled, and the pH was subsequently adjusted to be 9 to 9.5 with an 8% aqueous NaOH solution. The 8% aqueous NaOH solution was used in an amount of about 0.5 mL (1/2 to 1/3 equivalent) to 1 mL (equivalent).

As for the outer appearance of the resulting aluminum malate complex solution, the solution was transparent at one point when malic acid was used at 1/1 equivalent; however, the solution became slightly turbid during the heating and the turbidity was further increased by the subsequent pH adjustment. The solution was in the form of a turbid liquid when malic acid was used at 1/2 equivalent.

<Production of Glove Dipping Compositions>

To a 1-L beaker (manufactured by AS ONE Corporation, 105 mm in body diameter×150 mm in height), 220 g of each of the above-described commercially available XNBR latexes (solid content: 45%) was added, and the latex was subsequently diluted by adding thereto 200 g of water, followed by initiation of stirring. After preliminarily adjusting the pH to be about 9.9 using aqueous ammonia, a polycarbodiimide and zinc oxide, or a polycarbodiimide, zinc oxide and an aluminum complex, were added in the respective amounts shown in Tables 5 to 8 and 10 to 13. Further, 0.4 g of an antioxidant (trade name "CVOX-50", manufactured by Farben Technique (M) Sdn. Bhd.) and 1.5 g of titanium oxide (trade name "PW-601", manufactured by Farben Technique (M) Sdn. Bhd.) were added and, after adjusting the resulting solution with ammonia to have a pH of 10.5, water was further added thereto such that a solid concentration of 22% was attained, and the resultant was mixed for 24 hours. The amount of the thus obtained glove dipping composition was 486 g. It is noted here that the glove dipping composition was continuously stirred in the beaker until use.

The properties of the commercially available XNBRs were measured as follows.

<Amount of Acrylonitrile (AN) Residues and Amount of Unsaturated Carboxylic Acid (MMA) Residues>

Each elastomer (XNBR) was dried to prepare a film. This film was analyzed by FT-IR to determine the absorbance (Abs) at an absorption wavelength of 2,237 cm−1, which is attributed to acrylonitrile groups, and the absorbance (Abs) at an absorption wavelength of 1,699 cm−1, which is attributed to carboxylate groups, and the amount of acrylonitrile (AN) residues and the amount of unsaturated carboxylic acid (MMA) residues were determined.

The amount of acrylonitrile residues (%) was determined from a calibration curve that had been prepared in advance. The calibration curve was prepared using samples that were obtained by adding polyacrylic acid as an internal standard substance to the respective elastomers and had a known amount of acrylonitrile groups. The amount of unsaturated carboxylic acid residues was calculated using the following equation:

Amount of unsaturated carboxylic acid residues (% by weight)=[Abs(1,699 cm−1)/Abs(2,237 cm−1)]/0.2661

In this equation, the coefficient 0.2661 was calculated from a calibration curve that was prepared using a plurality of samples each having a known ratio of unsaturated carboxylate groups and acrylonitrile groups.

<Mooney Viscosity (ML(1+4)) (100° C.)>

To 200 ml of a saturated aqueous solution of a 4:1 mixture of calcium nitrate and calcium carbonate in a state of being stirred at room temperature, each elastomer (XNBR) latex was added dropwise using a pipette to precipitate a solid rubber. The thus precipitated solid rubber was taken out and repeatedly washed 10 times in about 1 L of ion-exchanged water with stirring, after which the solid rubber was dehydrated by squeezing and subsequently vacuum-dried (60° C., 72 hours), whereby a measurement rubber sample was prepared. The thus obtained measurement rubber sample was passed through 6-inch rolls having a roll temperature of 50° C. and a roll gap of about 0.5 mm several times until the rubber was settled, and the Mooney viscosity of this rubber sample was measured at 100° C. using a large-diameter rotator in accordance with JIS K6300-1:2001 "Rubber, Unvulcanized—Physical Property—Part 1: Determination of Mooney viscosity and pre-vulcanization characteristics with Mooney viscometer".

<MEK-Insoluble Content>

The MEK (methyl ethyl ketone)-insoluble (gel) component was quantified as follows. An XNBR latex dry sample in an amount of 0.2 g was placed in a mesh basket (80-mesh) whose weight had been measured, and the whole basket was immersed into 80 mL of MEK solvent in a 100-mL beaker. The beaker was subsequently capped with Parafilm and left to stand for 48 hours in a draft. Thereafter, the mesh basket was taken out of the beaker, hung in the draft, and dried for 1 hour. After vacuum-drying the basket at 105° C. for 1 hour, the weight thereof was measured, and the post-immersion weight of the XNBR latex dry sample was determined by subtracting the weight of the basket from the thus measured weight.

The content ratio of the MEK-insoluble component (insoluble content) was calculated using the following equation:

Content ratio of insoluble component (% by weight)=(Post-immersion weight (g)/Pre-immersion weight (g))×100

The XNBR latex dry sample was prepared as follows. That is, in a 500-mL bottle, an XNBR latex of interest was stirred for 30 minutes at a rotation speed of 500 rpm, and 14 g of the latex was subsequently weighed on a 180 mm×115 mm stainless-steel vat and dried overnight at normal temperature. This latex was further dried at 50° C. for 24 hours to prepare a cast film, which was subsequently cut into a 5-mm square to obtain an XNBR latex dry sample.

<Preparation of Liquid Coagulant>

After diluting 23.6 g of "S-9" (trade name, solid concentration: 25.46%, manufactured by Crestage Industry Sdn. Bhd.) by about 2-fold using a portion of 50 g of water that had been previously weighed, the thus diluted S-9 was slowly added as a dispersant to a solution obtained by dissolving 0.67 g of a wetting agent "TERIC 320" (trade name, manufactured by Huntsman Corporation) in 36.9 g of water. The whole amount of the S-9 was added while washing out the residual S-9 in the container with remaining water, and the resultant was stirred for 3 to 4 hours. Separately, in a 1-L beaker (manufactured by AS ONE Corporation, 105 mm in body diameter×150 mm in height), an aqueous calcium nitrate solution was prepared by dissolving 143.9 g of calcium nitrate tetrahydrate in 114.5 g of water, and the above-prepared S-9 dispersion was added thereto with stirring. The resultant was adjusted with 5% aqueous ammonia to have a pH of 8.5 to 9.5, and water was further added thereto such that the solid concentration of calcium nitrate as an anhydride and that of the S-9 were eventually 20% and 1.2%, respectively, whereby 500 g of a liquid coagulant was obtained. The thus obtained liquid coagulant was continuously stirred in the 1-L beaker until use.

<Production of Cured Films>

The liquid coagulant obtained above was heated to 50° C. with stirring, filtered through a 200-mesh nylon filter and then added to an immersion vessel, after which a plate made of ceramic (200 mm×80 mm×3 mm; hereinafter, referred to as "ceramic plate") that had been washed and then heated to 60° C. was immersed therein. Specifically, once a tip of the ceramic plate was brought into contact with the surface of the liquid coagulant, the ceramic plate was immersed to a position of 18 cm from the tip over a period of 4 seconds, and this immersed state was maintained for 4 seconds before pulling out the ceramic plate over a period of 3 seconds. Then, the liquid coagulant adhering to the surface of the ceramic plate was promptly shaken off, and the surface of the ceramic plate was dried. The thus dried ceramic plate was heated again to 60° C. in preparation for the subsequent immersion in a glove dipping composition.

The glove dipping compositions obtained above were each directly filtered through a 200-mesh nylon filter at room temperature and then added to an immersion vessel, after which the above-described 60° C. ceramic plate to which the liquid coagulant had been adhered was immersed therein. Specifically, the ceramic plate was immersed over a period of 6 seconds, maintained for 4 seconds, and then pulled out over a period of 3 seconds. The ceramic plate was held in the air until the glove dipping composition no longer dripped, and latex droplets adhering to the tip were lightly shaken off.

The ceramic plate immersed in the glove dipping composition was left to stand at room temperature (23° C.) for 1 minute (gelling) and subsequently leached with 50° C. warm water for 5 minutes. Thereafter, the ceramic plate was dried at 70° C. for 1 minute and then heat-cured at 120° C. for 30 minutes (curing).

The thus obtained cured film (average thickness: 0.07 mm) was cleanly peeled off from the ceramic plate and stored at a temperature of 23° C.±2° C. and a humidity of 50%±10% until being subjected to the physical property tests.

<Evaluation of Cured Films>

(1) Tensile Strength

From each cured film, a #5 dumbbell test piece according to JIS K6251 was cut out, and the tensile strength (MPa) thereof was measured using a TENSILON universal tensile tester RTC-1310A manufactured by A&D Co., Ltd. at a test rate of 500 mm/min, a chuck distance of 75 mm and a gauge mark distance of 25 mm.

(2) Fatigue Durability

A #1 dumbbell test piece according to JIS K6251 was cut out from each cured film and immersed in an artificial sweat solution (which contained 20 g of sodium chloride, 17.5 g of ammonium chloride, 17.05 g of lactic acid and 5.01 g of acetic acid in 1 liter and whose pH had been adjusted to 4.7 with sodium hydroxide), and the fatigue durability was evaluated using the above-described durability test apparatus.

Figure 7:
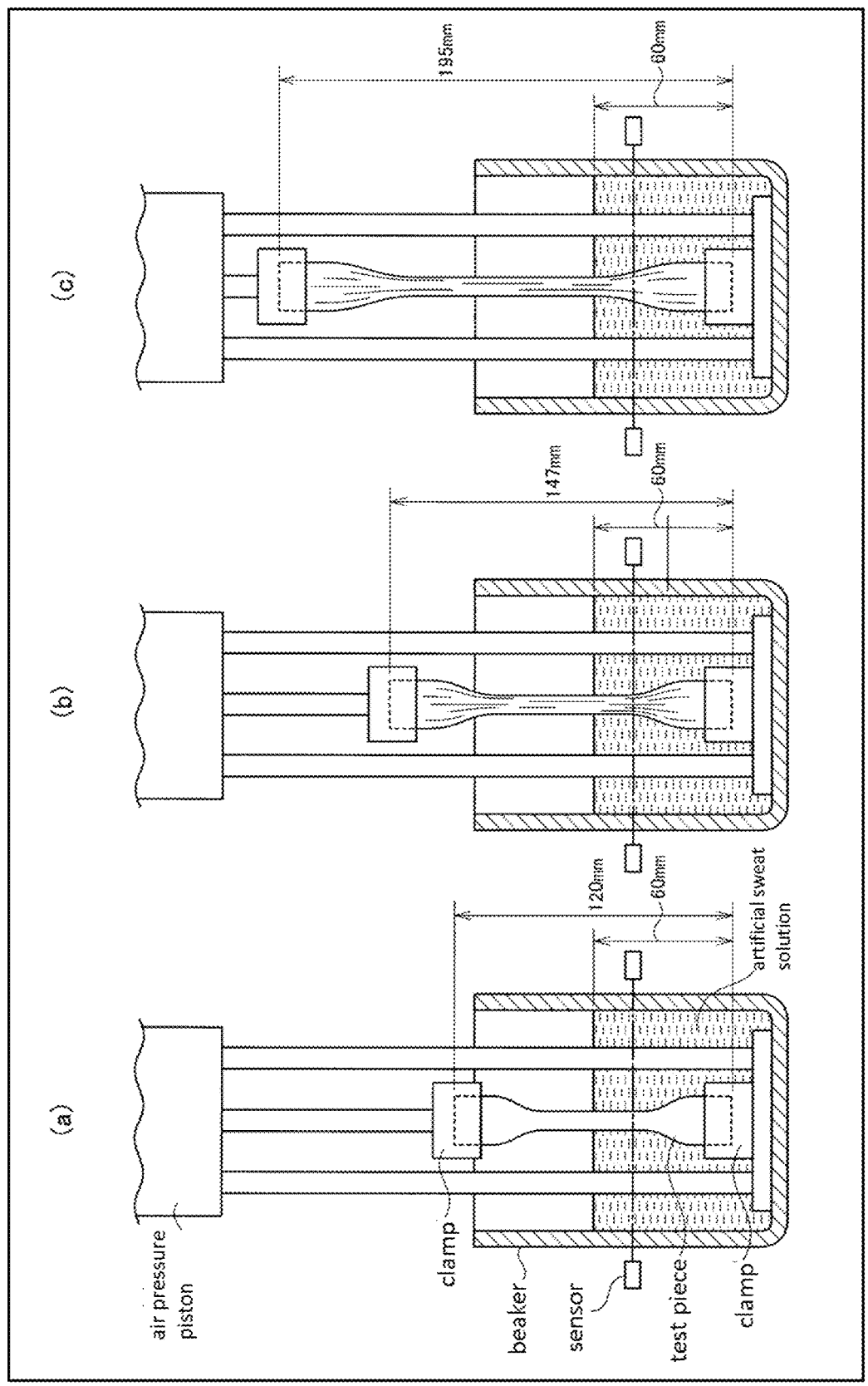
FIG. 7 shows cross-sectional views that schematically illustrate one example of a fatigue durability test apparatus.

That is, using the apparatus illustrated in FIG. 7, the dumbbell test piece of 120 mm in length was held by a fixed chuck and a mobile chuck at 15 mm away from each of the two ends, and the test piece was immersed in the artificial sweat solution up to 60 mm from the lower end on the side of the fixed chuck. After moving the mobile chuck to a minimum position (relaxed state) where the test piece had a length of 147 mm (123%) and maintaining the mobile chuck at this position for 11 seconds, the mobile chuck was moved to a maximum position (elongated state) where the test piece had a length of 195 mm (163%) and then moved back to the minimum position (relaxed state) in 1.5 seconds. A cycle test was performed taking these moving operations as one cycle. The fatigue durability time (minutes) was determined by multiplying the duration of each cycle, which was 12.5 seconds, by the number of the cycles until the test piece was torn.

(Judgment of Reduction in Tensile Strength of Cured Films in Artificial Sweat Solution>

In Tables 5 to 7, with regard to the effect of inhibiting a reduction in tensile strength caused by immersion in an artificial sweat solution, evaluations of "x", "o" and "@" were given to poor inhibition, good inhibition and particularly good inhibition, respectively; however, these evaluations were not obtained by actual measurement of the respective cured films. The effect was judged based on the results of experimentally measuring the reduction in tensile strength caused by 20-hour immersion in the artificial sweat solution for gloves containing Ca, Zn and Al (Table 1, FIG. 2 and FIG. 3).

(Judgment of Organic Solvent Impermeability of Cured Films)

In Tables 5 to 7, with regard to the organic solvent impermeability, evaluations of "x", "○" and "⊚" were given to poor organic solvent impermeability, good organic solvent impermeability and particularly good organic solvent impermeability, respectively; however, these evaluations were not obtained by actual measurement of the respective cured films. The organic solvent impermeability was judged based on the results of evaluating the swelling of gloves containing Ca, Zn and Al against organic solvents in terms of the Hansen solubility parameters (HSP) (Table 3).

The fact that Zn is superior to Ca in terms of organic solvent impermeability is also seen from the comparison of the performances of the glove of Example 30.

<Production of Gloves>

Gloves were produced in accordance with the method described in FIGS. 6-1 and 6-2.

(5) Experiments for Verifying Improvements Attained by Zinc Oxide and Aluminum Complex in Initial Tensile Strength, Reduction of Tensile Strength in Artificial Sweat Solution and Organic Solvent Impermeability In Examples 6 to 18 shown in Table 5 below, NL120H as an XNBR, one of four polycarbodiimides that mainly contained E-03A and had a polycarbodiimide equivalent of 440 or less and zinc oxide were added to each dipping composition. In some of these Examples, an aluminum complex was further added. Using these dipping compositions, cured films were each produced in accordance with the above-described <Production of Cured Films>, and their physical properties were measured. The results thereof are shown in Table 6.

According to the results shown in Table 6, in all of these Examples, the tensile strength was 20 MPa or higher, the fatigue durability was 200 minutes or longer, and good inhibition of a reduction in the tensile strength in the artificial sweat solution as well as good organic solvent impermeability were attained with no problem.

As for Examples 6 to 9, it was shown that an addition of mere 0.5% by weight of E-03A to the dipping composition can yield a fatigue durability higher than that (200 to 400 minutes or so) of a conventional XNBR glove, that an appropriate tensile strength can be attained even when zinc oxide is added in an amount of 0.25% by weight, and that the tensile strength can be controlled to be enhanced by increasing the amount of added zinc oxide.

As for Examples 10 to 13 where E-03A was added in an amount of 1% by weight and the amount of zinc oxide was increased in the same manner as described above, the same tendencies were observed as in Examples 6 to 9.

In Examples 14 and 15, in addition to 1% by weight of E-03A and 0.5% by weight of zinc oxide that were added to the respective dipping compositions, an aluminum complex was further added in an amount of 0.2% by weight (Example 14) or 0.4% by weight (Example 15). Referring to the results of these Examples, it was found that the organic solvent impermeability is enhanced by adding an aluminum complex to a dipping composition.

Examples 16 to 18 show the results of experiments where one of three polycarbodiimides other than E-03A (E-05, V-04 and V-02-L2) was used. These polycarbodiimides all have a polycarbodiimide equivalent of 440 or less and a high polymerization degree of carbodiimide groups. Good results were obtained in all of these Examples.

Figure 3:
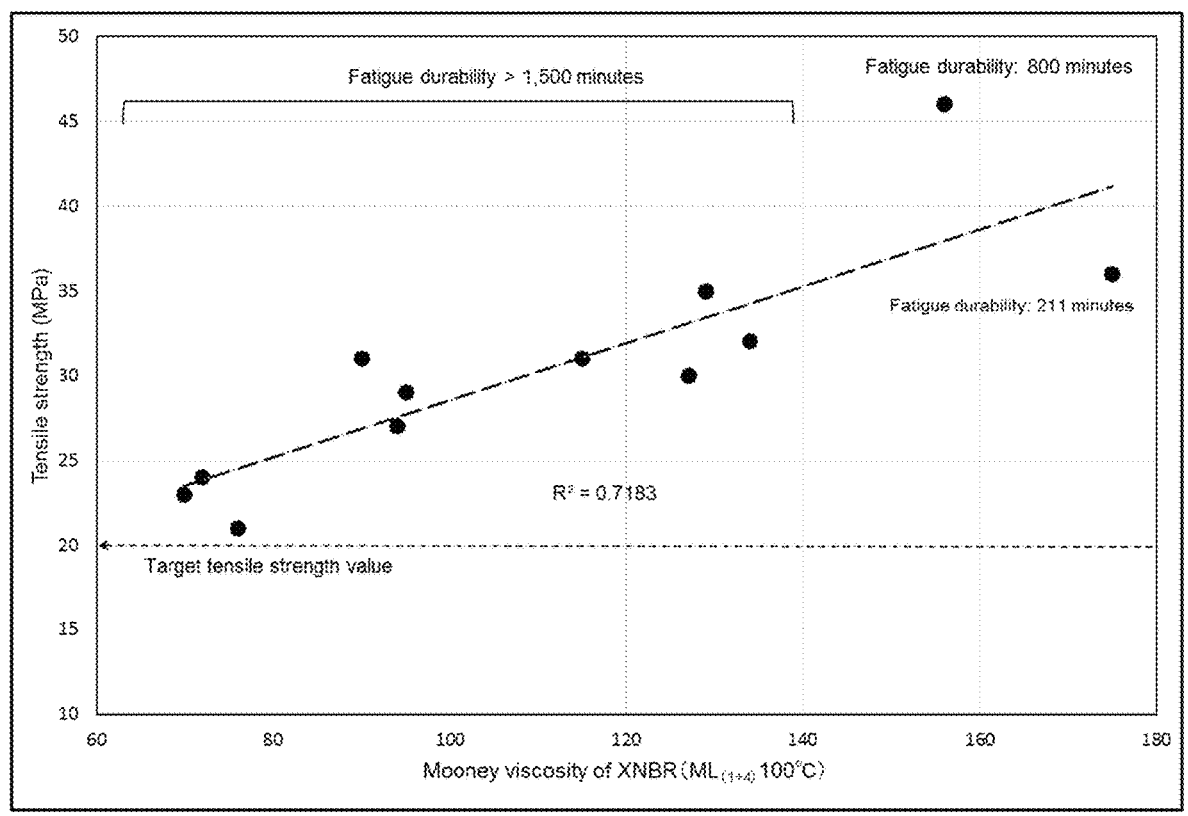
FIG. 3 is a graph showing the relationship between the Mooney viscosity of elastomers and the tensile strength.

(6) Experiments for Verifying Relationships Between Mooney Viscosity of Elastomers (XNBARs) and Tensile Strength and Fatigue Durability of Films In Examples 19 to 29 and Reference Example 8 shown in Table 6 below, one of almost all commercially available XNBRs, 1% by weight of E-03A and 0.5% by weight of zinc oxide were added to the respective dipping compositions. In Table 6, the Mooney viscosity of the elastomers (XNBRs) increases from the left to the right. Using these dipping compositions, cured films were each produced in accordance with the above-described <Production of Cured Films>, and their physical properties were measured. The results thereof are shown in Table 6. Referring to the results shown in Table 6, satisfactory physical properties demanded by the present inventors were attained in almost all of Examples 19 to 29. However, as shown in Reference Example 8, it was found that the fatigue durability was reduced when the elastomer (XNBR) had a very high Mooney viscosity of 175. FIG. 3 shows the results of plotting the tensile strength on the ordinate and the Mooney viscosity of the respective elastomers (XNBRs) on the abscissa.

TABLE 5

Improvements Attained by Zinc Oxide and Aluminum Complex in Initial Tensile Strength, Reduction of Tensile Strength in Artificial Sweat Solution and Organic Solvent Impermeability

|  |  | Example 6 | Example 7 | Example 8 | Example 9 | Example 10 | Example 11 | Example 12 |
|---|---|---|---|---|---|---|---|---|
| XNBR | Type | NL120H | NL120H | NL120H | NL120H | NL120H | NL120H | NL120H |
|  | Mooney viscosity ($ML_{(1+4)}$ 100° C.) | 111 | 111 | 111 | 111 | 111 | 111 | 111 |
|  | MEK-insoluble content (% by weight) | 5.6 | 5.6 | 5.6 | 5.6 | 5.6 | 5.6 | 5.6 |
|  | Amount of MMA (COOH) (% by weight) | 5.3 | 5.3 | 5.3 | 5.3 | 5.3 | 5.3 | 5.3 |
|  | Amount of AN (% by weight) | 28 | 28 | 28 | 28 | 28 | 28 | 28 |
|  | Butadiene (% by weight) | 66.7 | 66.7 | 66.7 | 66.7 | 66.7 | 66.7 | 66.7 |
| Crosslinking agent | $Ca^{2+}$ (coagulant) (○: present X: absent) | ○ | ○ | ○ | ○ | ○ | ○ | ○ |
|  | Polycarbodiimide Type | E-03A | E-03A | E-03A | E-03A | E-03A | E-03A | E-03A |
|  | Added amount (% by weight) | 0.5 | 0.5 | 0.5 | 0.5 | 1 | 1 | 1 |
|  | Amount of added ZnO (% by weight) | 0.25 | 0.5 | 0.75 | 1 | 0.25 | 0.5 | 0.75 |
|  | Amount of added Al complex (% by weight) | 0 | 0 | 0 | 0 | 0 | 0 | 0 |
| pH | Adjusted value | 10.5 | 10.5 | 10.5 | 10.5 | 10.5 | 10.5 | 10.5 |
|  | Modifier | $NH_3$ | $NH_3$ | $NH_3$ | $NH_3$ | $NH_3$ | $NH_3$ | $NH_3$ |
| Physical properties | Tensile stength (MPa) (target value ≥ 20 MPa) | 34 | 36 | 38 | 40 | 36 | 39 | 46 |
|  | Fatigue durability (min) (target value ≥ 200 min) | 500 | 420 | 823 | 900 | >1,500 not broken | >1,500 not broken | >1,500 not broken |
|  | Inhibition of reduction in tensile strength in artificial sweat solution | ○ | ○ | ○ | ○ | ○ | ○ | ○ |
|  | Organic solvent impermeability | ○ | ○ | ○ | ○ | ○ | ○ | ○ |

|  |  | Example 13 | Example 14 | Example 15 | Example 16 | Example 17 | Example 18 |
|---|---|---|---|---|---|---|---|
| XNBR | Type | NL120H | NL120H | NL120H | NL120H | NL120H | NL120H |
|  | Mooney viscosity ($ML_{(1+4)}$ 100° C.) | 111 | 111 | 111 | 111 | 111 | 111 |
|  | MEK-insoluble content (% by weight) | 5.6 | 5.6 | 5.6 | 5.6 | 5.6 | 5.6 |
|  | Amount of MMA (COOH) (% by weight) | 5.3 | 5.3 | 5.3 | 5.3 | 5.3 | 5.3 |
|  | Amount of AN (% by weight) | 28 | 28 | 28 | 28 | 28 | 28 |
|  | Butadiene (% by weight) | 66.7 | 66.7 | 66.7 | 66.7 | 66.7 | 66.7 |
| Crosslinking agent | $Ca^{2+}$ (coagulant) (○: present X: absent) | ○ | ○ | ○ | ○ | ○ | ○ |
|  | Polycarbodiimide Type | E-03A | E-03A | E-03A | E-05 | V-04 | V-02-L2 |
|  | Added amount (% by weight) | 1 | 1 | 1 | 1 | 1 | 1 |
|  | Amount of added ZnO (% by weight) | 1 | 0.5 | 0.5 | 0.5 | 0.5 | 0.5 |
|  | Amount of added Al complex (% by weight) | 0 | 0.2 | 0.4 | 0 | 0 | 0 |
| pH | Adjusted value | 10.5 | 10.5 | 10.5 | 10.5 | 10.5 | 10.5 |
|  | Modifier | $NH_3$ | $NH_3$ | $NH_3$ | $NH_3$ | $NH_3$ | $NH_3$ |
| Physical properties | Tensile stength (MPa) (target value ≥ 20 MPa) | 50 | 45 | 50 | 39 | 35 | 37 |
|  | Fatigue durability (min) (target value ≥ 200 min) | >1,500 not broken | >1,500 not broken | >1,500 not broken | >1,500 not broken | >1,500 not broken | >1,500 not broken |
|  | Inhibition of reduction in tensile strength in artificial sweat solution | ○ | ◎ | ◎ | ○ | ○ | ○ |
|  | Organic solvent impermeability | ○ | ◎ | ◎ | ○ | ○ | ○ |

Sample: a film (thickness: 70 μm) formed on a ceramic plate, Gelling conditions: at 23° C. for 1 minute, no humectant
Physical properties: particularly good = "◎", good = "○", poor = "X"
For the pH adjustment the respective XNBRs and crosslinking agents were mixed for 24 hours, and the coagulant was 20%-by-weight calcium nitrate and mixed for 24 hours.

From the results shown in Table 6 and FIG. 3, the present inventors believe that the XNBR used in the embodiments of the present invention should suitably have a Mooney viscosity of 70 to 160 or so.

Comparative Examples mean that excellent fatigue durability and tensile strength were attained by narrowing down the requirements for the Mooney viscosity of the XNBR and for the polycarbodiimide. However, in these cases where only

TABLE 6

Relationships between Mooney Viscosity of Elastomers (XNBRs) and Tensile Strength and Fatigue Durability of Films

|  |  | Example 19 | Example 20 | Example 21 | Example 22 | Example 23 | Example 24 |
|---|---|---|---|---|---|---|---|
| XNBR | Type | XVT-LA | NBL201B | KNL860 | LX550L | NL105 | X6311 |
|  | Mooney viscosity ($ML_{(1+4)}$ 100° C.) | 70 | 72 | 76 | 90 | 94 | 95 |
|  | Amount of MEK-insoluble component (gel) (% by weight) | 52 | 41 | 50 | 47 | 0.6 | 60 |
|  | Amount of MMA (COOH) (% by weight) | 2.7 | 3.1 | 1.5 | 4 | 5.8 | 3.1 |
|  | Amount of AN (% by weight) | 29 | 26 | 26 | 26 | 26 | 26 |
|  | Amount of butadiene (% by weight) | 68.3 | 70.9 | 72.5 | 70 | 68.2 | 70.9 |
| Crosslinking agent | $Ca^{2+}$ (coagulant) (○: present X: absent) | ○ | ○ | ○ | ○ | ○ | ○ |
|  | Polycarbodiimide Type | E-03A | E-03A | E-03A | E-03A | E-03A | E-03A |
|  | Added amount (% by weight) | 1 | 1 | 1 | 1 | 1 | 1 |
|  | Amount of added ZnO (% by weight) | 0.5 | 0.5 | 0.5 | 0.5 | 0.5 | 0.5 |
| pH | Adjusted value | 10.5 | 10.5 | 10.5 | 10.5 | 10.5 | 10.5 |
|  | Modifier | $NH_3$ | $NH_3$ | $NH_3$ | $NH_3$ | $NH_3$ | $NH_3$ |
| Physical properties | Tensile strength (MPa) (target value ≥ 20 MPa) | 23 | 24 | 21 | 31 | 27 | 29 |
|  | Fatigue durability (min) (target value ≥ 200 min) | >1,500 not broken | >1,500 not broken | >1,500 not broken | >1,500 not broken | >1,500 not broken | >1,500 not broken |
|  | Reduction in tensile strength in artificial sweat solution | ○ | ○ | ○ | ○ | ○ | ○ |
|  | Organic solvent impermeability | ○ | ○ | ○ | ○ | ○ | ○ |

|  |  | Example 25 | Example 26 | Example 27 | Example 28 | Example 29 | Reference Example 8 |
|---|---|---|---|---|---|---|---|
| XNBR | Type | NL107 | 203A | 6338 | NL111 | 746SXL | N552 |
|  | Mooney viscosity ($ML_{(1+4)}$ 100° C.) | 115 | 127 | 129 | 134 | 156 | 175 |
|  | Amount of MEK-insoluble component (gel) (% by weight) | 58 | 60 | 46 | 51 | 64 | 95 |
|  | Amount of MMA (COOH) (% by weight) | 5.5 | 2.3 | 4 | 6.5 | 2.9 | 8.3 |
|  | Amount of AN (% by weight) | 27 | 26 | 32 | 35 | 28 | 35 |
|  | Amount of butadiene (% by weight) | 67.5 | 71.7 | 64 | 58.5 | 69.1 | 56.7 |
| Crosslinking agent | $Ca^{2+}$ (coagulant) (○: present X: absent) | ○ | ○ | ○ | ○ | ○ | ○ |
|  | Polycarbodiimide Type | E-03A | E-03A | E-03A | E-03A | E-03A | E-03A |
|  | Added amount (% by weight) | 1 | 1 | 1 | 1 | 1 | 1 |
|  | Amount of added ZnO (% by weight) | 0.5 | 0.5 | 0.5 | 0.5 | 0.5 | 0.5 |
| pH | Adjusted value | 10.5 | 10.5 | 10.5 | 10.5 | 10.5 | 10.5 |
|  | Modifier | $NH_3$ | $NH_3$ | $NH_3$ | $NH_3$ | $NH_3$ | $NH_3$ |
| Physical properties | Tensile strength (MPa) (target value ≥ 20 MPa) | 31 | 30 | 35 | 32 | 46 | 36 |
|  | Fatigue durability (min) (target value ≥ 200 min) | >1,500 not broken | >1,500 not broken | >1,500 not broken | >1,500 not broken | 800 | 211 |
|  | Reduction in tensile strength in artificial sweat solution | ○ | ○ | ○ | ○ | ○ | ○ |
|  | Organic solvent impermeability | ○ | ○ | ○ | ○ | ○ | ○ |

Sample: a film (thickness: 70 μm) formed on a ceramic plate, Gelling conditions: at 23° C. for 1 minute, no humectant
Physical properties: particularly good = "⊙", good = "○", poor = "X"
For the pH adjustment, the respective XNBRs and crosslinking agents were mixed for 24 hours, and the coagulant was 20%-by-weight calcium nitrate and mixed for 24 hours.

(7) Verification of Physical Properties of Comparative Examples (Cases where Neither Zinc Oxide Nor Aluminum Complex was Contained in Dipping Composition) and Reference Examples (e.g., Cases where Carbodiimide Crosslinking Agent Having High Equivalent was Used)

In Comparative Examples 5 and 6 shown in Table 7, NL-120H was used as the elastomer (XNBR) contained in the respective dipping compositions. Using the dipping compositions, cured films were each produced in accordance with the above-described <Production of Cured Films>, and their physical properties were measured. The results thereof are shown in Table 7.

Comparative Examples 5 and 6 are cases where 1% by weight or 0.5% by weight of E-03A was incorporated into each dipping composition without any zinc oxide or aluminum complex, and these Comparative Examples represent the physical properties achieved by the gloves of the present inventors that are obtained with the use of only the polycarbodiimide as a crosslinking agent. The results of these Comparative Examples mean that excellent fatigue durability and tensile strength were attained by narrowing down the requirements for the Mooney viscosity of the XNBR and for the polycarbodiimide. However, in these cases where only the polycarbodiimide was used as a crosslinking agent, it was found that calcium is likely to elute into the artificial sweat solution since another mode of crosslinking is dependent on calcium (Ca), that the organic solvents easily permeates through the gloves since ionic bonds are weaker than Zn crosslinks and Al crosslinks, and that, therefore, there is a problem in terms of reduction in tensile strength in an artificial sweat solution as well as the organic solvent impermeability.

In Reference Examples 9 to 14 shown in Table 7, NL-120H was used as the elastomer (XNBR) contained in the respective dipping compositions as in Comparative Examples 5 and 6. Using these dipping compositions, cured films were each produced in accordance with the above-described <Production of Cured Films>, and their physical properties were measured. The results thereof are shown in Table 7.

Reference Example 9 is a case where only Ca crosslinks were incorporated, and it was shown that Ca crosslinks contribute to the tensile strength but they make substantially no contribution to the fatigue durability.

In Reference Example 10, the capability of the polycarbodiimide alone was verified by adjusting the pH of the dipping composition to be 7 and thereby inhibiting Ca crosslinking. As a result, it was shown that the crosslinks formed by the polycarbodiimide alone contribute to the fatigue durability but not to the tensile strength.

In Reference Examples 11 to 14, since neither zinc oxide nor an aluminum complex was incorporated as a crosslinking agent, the tensile strength was reduced after the immersion in the artificial sweat solution and the organic solvent impermeability was poor in all of these Examples.

Figure 4:
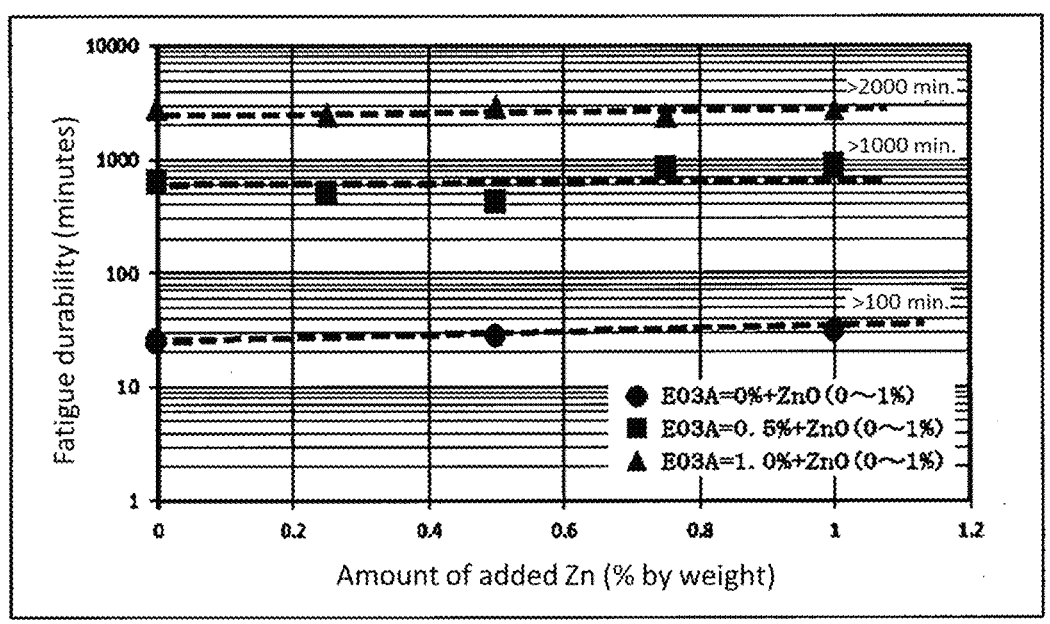
FIG. 4 is a graph showing the fatigue durability levels obtained by changing the addition of zinc oxide and a polycarbodiimide in a logarithmic scale (irrespective of a change in the amount of added zinc oxide).

From the results of FIG. 4, it was found that, as compared to those cases where no crosslinking agent was added or only zinc oxide was added as a crosslinking agent to the dipping compositions, the fatigue durability was noticeably improved when the polycarbodiimide was added to the dipping compositions. In addition, it was found that the fatigue durability was further improved when the amount of the polycarbodiimide was increased.

(8) Confirmation of Improvement in Organic Solvent Impermeability and Fatigue Durability by Addition of Zinc Oxide The formulations of the dipping compositions used in Example 30 and Comparative Example 7 are shown in Table

TABLE 7

Comparative Examples (neither ZnO nor Al was incorporated) and Reference Examples (e.g., cases where a carbodiimide crosslinking agent having a high equivalent was used)

| | | Comparative Example 5 | Comparative Example 6 | Reference Example 9 | Reference Example 10 |
|---|---|---|---|---|---|
| XNBR | Type | NL120H | NL120H | NL120H | NL120H |
| | Mooney viscosity (ML$_{(1+4)}$ 100° C.) | 111 | 111 | 111 | 111 |
| | MEK-insoluble content (% by weight) | 5.6 | 5.6 | 5.6 | 5.6 |
| | Amount of MMA (COOH) (% by weight) | 5.3 | 5.3 | 5.3 | 5.3 |
| | Amount of AN (% by weight) | 28 | 28 | 28 | 28 |
| | Butadiene (% by weight) | 66.7 | 66.7 | 66.7 | 66.7 |
| Crosslinking agent | Ca$^{2+}$ (coagulant) (○: present, X: absent) | ○ | ○ | ○ | X |
| | Polycarbodiimide Type | E-03A | E-03A | — | E-02 |
| | Added amount (% by weight) | 1 | 0.5 | 0 | 3 |
| | Amount of added ZnO (% by weight) | 0 | 0 | 0 | 0 |
| | Amount of added Al complex (% by weight) | 0 | 0 | 0 | 0 |
| pH | Adjusted value | 10.5 | 10.5 | 10.5 | 7 |
| | Modifier | NH$_3$ | NH$_3$ | NH$_3$ | HCl |
| Physical properties | Tensile strength (MPa) (target value ≥ 20 MPa) | 32 | 32 | 26 | 13 |
| | Fatigue durability (min) (target value ≥ 200 min) | >1,500 not broken | 650 | 51 | 800 |
| | Inhibition of reduction in tensile strength in artificial sweat solution | X | X | X | X |
| | Organic solvent impermeability | X | X | X | X |

| | | Reference Example 11 | Reference Example 12 | Reference Example 13 | Reference Example 14 |
|---|---|---|---|---|---|
| XNBR | Type | NL120H | NL120H | NL120H | NL120H |
| | Mooney viscosity (ML$_{(1+4)}$ 100° C.) | 111 | 111 | 111 | 111 |
| | MEK-insoluble content (% by weight) | 5.6 | 5.6 | 5.6 | 5.6 |
| | Amount of MMA (COOH) (% by weight) | 5.3 | 5.3 | 5.3 | 5.3 |
| | Amount of AN (% by weight) | 28 | 28 | 28 | 28 |
| | Butadiene (% by weight) | 66.7 | 66.7 | 66.7 | 66.7 |
| Crosslinking agent | Ca$^{2+}$ (coagulant) (○: present, X: absent) | ○ | ○ | ○ | ○ |
| | Polycarbodiimide Type | V-02 | E-02 | E-02 | E-02 |
| | Added amount (% by weight) | 1 | 3 | 2 | 1 |
| | Amount of added ZnO (% by weight) | 0 | 0 | 0 | 0 |
| | Amount of added Al complex (% by weight) | 0 | 0 | 0 | 0 |
| pH | Adjusted value | 10.5 | 10.5 | 10.5 | 10.5 |
| | Modifier | NH$_3$ | NH$_3$ | NH$_3$ | NH$_3$ |
| Physical properties | Tensile strength (MPa) (target value ≥ 20 MPa) | 30 | 32 | 35 | 35 |
| | Fatigue durability (min) (target value ≥ 200 min) | 23 | >1,500 not broken | 329 | 120 |
| | Inhibition of reduction in tensile strength in artificial sweat solution | X | X | X | X |
| | Organic solvent impermeability | X | X | X | X |

Sample: a film (thickness: 70 μm) formed on a ceramic plate; Gelling was performed at 23° C. for 1 minute with no humectant in Comparative Examples 5 and 6, or at 50° C. for 20 minutes with no humectant in Reference Examples 9 to 14.
Physical properties: particularly good = "⊚", good = "○", poor = "X"
For the pH adjustment, the respective XNBRs and crosslinking agents were mixed for 24 hours, and the coagulant was 20%-by-weight calcium nitrate and mixed for 24 hours.

The experimental results of above (5) (Examples 6 to 13) and the experimental results of above (7) (Comparative Examples 5 and 6) as well as the results of testing the fatigue durability of the cured films obtained by adding no crosslinking agent or adding only zinc oxide (0.5% by weight or 1% by weight) as a crosslinking agent to the respective dipping compositions are summarized in FIG. 4.

8 below. Using these dipping compositions, cured films were each produced in accordance with the above-described <Production of Cured Films>, and their physical properties were measured. The results thereof are shown in Table 8. In this experiment, the performance was compared between a glove that was produced with an addition of a polycarbodiimide and zinc oxide to the dipping composition and a glove that was crosslinked by using only a polycarbodiimide as a crosslinking agent without adding zinc oxide to the dipping composition.

meability. The level 2 means that a period of longer than 30 minutes to 60 minutes is required for the chemical substance to permeate through the rubber glove.

TABLE 8

Improvement in Organic Solvent Impermeability and Fatigue Durability by Addition of Zinc Oxide

| | | | Example 30 | Comparative Example 7 |
|---|---|---|---|---|
| XNBR | Type | | 120H | 120H |
| | Mooney viscosity ($ML_{(1+4)}$ 100° C.) | | 111 | 111 |
| | MEK-insoluble content (% by weight) | | 5.6 | 5.6 |
| | Amount of MMA (COOH) (% by weight) | | 5.3 | 5.3 |
| | Amount of AN (% by weight) | | 28 | 28 |
| | Amount of butadiene (% by weight) | | 66.7 | 66.7 |
| Crosslinking agent | Polycarbodiimide crosslinking agent | Type | E-03A | E-03A |
| | | Added amount (% by weight) | 1 | 1 |
| | Amount of added ZnO (% by weight) | | 0.5 | 0 |
| Glove physical properties | Thickness (μm) | | 86 | 77 |
| | Breaking strength | (N) | 14.3 | 10.8 |
| | | (MPa) | 55.3 | 46.8 |
| | Elongation (%) | | 567.6 | 607 |
| | Modulus (MPa) | 300% | 9.52 | 5.97 |
| | | 500% | 35.95 | 19.72 |
| | Fatigue durability (finger crotch part 260%) (times)[Note1] | | 504 | 86 |
| | Organic solvent impermeability (min) | Hexane | 26 | 15.5 |
| | | IPA | 24 | 12.1 |

Sample: a glove, Gelling conditions: at 50° C. for 3 minutes, no humectant

[Note1] Fatigue durability: different from other fatigue durability test in that a glove was subjected to repeated operations of 260% elongation and relaxation and the number of the operations performed until a finger crotch part of the glove was torn was measured.

From the results shown in Table 8, the followings were found.

(I) Physical Properties

For the gloves produced in Example 30 and Comparative Example 7, the breaking strength was measured in accordance with the EN455 standard, and other physical properties were measured in accordance with the ASTM standards. As a result, the glove of Example 30 had a breaking strength of 55.3 MPa, a 300% modulus of 9.52 MPa, a 500% modulus of 35.95 MPa and an elongation at break of 567.6%, and these physical properties were superior to those of Comparative Example 7.

(II) Fatigue Durability

As a result of the property test performed on a finger crotch part of the glove of Example 30, the fatigue durability was found to be 504 times, which was much better than 86 times of Comparative Example 7.

(III) The Organic Solvent Impermeability of Example 30 was 26.0 Minutes for Hexane and 24.0 Minutes for IPA, Both of which are Very Good Results.

(IV) Chemical Impermeability

In Example 30, the closer to the performance level 2 defined by the EN374 standard "Protective gloves against chemicals and micro-organisms" (JIS T8116 "Protective gloves for use against chemicals"), the superior was the organic solvent impermeability.

(9) Regarding the Performance Levels Based on EN374

In EN374, as shown in Table 9 below, the time required for a chemical substance to permeate through a rubber glove is represented by the performance levels of chemical imper-

TABLE 9

Chemical Impermeability Performance Level (EN374 Standard)

| | Performance level | | | | | |
|---|---|---|---|---|---|---|
| | 0 | 1 | 2 | 3 | 4 | 5 | 6 |
| Permeation time (min) | <10 | 10 | 30 | 60 | 120 | 240 | >480 |

(10) Confirmation of Improvement on Reduction in Physical Properties Caused by Immersion in Artificial Sweat Solution Table 10 relates to the experimental results showing that an addition of zinc oxide and an aluminum complex as crosslinking agents improved the problem verified in Table 2 that the glove obtained using a dipping composition containing only a polycarbodiimide as a crosslinking agent (Comparative Example 1) had a larger reduction in tensile strength in an artificial sweat solution than other gloves (Reference Examples 1 to 3).

In Examples 31 to 34, the respective dipping compositions contained NL120H as an elastomer (XNBR), and 0.5% by weight of a polycarbodiimide (E-03A) as a crosslinking agent and 0.5% by weight of zinc oxide were added thereto (Example 31), and 0.3% by weight of an aluminum complex was further added thereto (Examples 32 to 34).

As the aluminum complex, an aluminum citrate complex (Example 32), an aluminum malate complex (Example 33) or an aluminum hydroxide complex (Example 34) was used.

Using the respective dipping compositions, cured films were each produced in accordance with the above-described <Production of Cured Films>, and their physical properties were measured. The results thereof are shown in Table 10.

According to the results, by the addition of zinc oxide (Example 31), the tensile strength retention rate after the immersion in 23° C. artificial sweat solution was largely improved from 48% in Comparative Example 1 to 63%.

In addition, in those cases where an aluminum complex was added (Examples 32 to 34), the tensile strength retention rate after immersion in artificial sweat solution was largely improved both at 23° C. and 50° C.

Moreover, when the metal content was measured for the cured films of these Examples before and after the immersion in the artificial sweat solution, it was found that calcium most readily eluted and zinc and aluminum were unlikely to elute. Particularly, it was found that hardly any aluminum eluted even under such a severe condition where the temperature of the artificial sweat solution was 50° C.

Furthermore, in all of these Examples, a film having sufficient performance was prepared even with a smaller amount of the crosslinking agent than in other gloves (Table 2, Reference Examples 1 to 3).

dipping compositions were both fixed at 0.5% by weight, the amount of a citrate complex as an aluminum complex was adjusted in a range of 0 to 0.5% by weight, and the performance thereof was examined.

In Examples 39 and 40, the aluminum complex used in Example 38 was changed to a malate complex and a hydroxide complex, respectively. As a result, it was found that a glove having sufficient properties was obtained in all of these Examples.

With regard to the addition of an aluminum complex, it is effective particularly for improving the inhibition of a reduction in tensile strength in an artificial sweat solution as well as the organic solvent impermeability. As for the type of the

TABLE 10

Improvement on Reduction in Physical Properties Caused by Immersion in Artificial Sweat Solution

|  |  |  |  | Example 31 | Example 32 | Example 33 | Example 34 |
|---|---|---|---|---|---|---|---|
| XNBR |  | Type |  | NL120H | NL120H | NL120H | NL120H |
|  |  | Mooney viscosity ($ML_{(1+4)}$ 100° C.) |  | 111 | 111 | 111 | 111 |
|  |  | MEK-insoluble content (% by weight) |  | 5.6 | 5.6 | 5.6 | 5.6 |
|  |  | Amount of MMA (COOH) (% by weight) |  | 5.3 | 5.3 | 5.3 | 5.3 |
|  |  | Amount of AN (% by weight) |  | 28 | 28 | 28 | 28 |
| Crosslinking agent |  | $Ca^{2+}$ (coagulant) (○: present, X: absent) |  | ○ | ○ | ○ | ○ |
|  | Poly carbodiimide |  | Type | E-03A | E-03A | E-03A | E-03A |
|  |  | Added amount (% by weight) |  | 0.5 | 0.5 | 0.5 | 0.5 |
|  |  | Amount of added ZnO (% by weight) |  | 0.5 | 0.5 | 0.5 | 0.5 |
|  | Al complex |  | Type | — | citrate complex | malate complex | hydroxide complex |
|  |  | Added amount (% by weight) |  | — | 0.3 | 0.3 | 0.3 |
| Physical properties |  | Tensile strength (MPa) (target value ≥ 20 MPa) |  | 40.3 | 43.3 | 42.6 | 38.3 |
|  |  | Elongation (%) |  | 503 | 497 | 499 | 472 |
|  | Inhibition of reduction in physical properties in artificial sweat solution | Tensile strength (MPa) after 20-hour immersion Retention rate (%) in parentheses | Water, at 50° C. | 45.2 (112) | 35.9 (83) | 40.7 (96) | 38.5 (101) |
|  |  |  | Artificial sweat solution, at 23° C. | 25.5 (63) | 31.5 (73) | 29.5 (69) | 25.2 (66) |
|  |  |  | Artificial sweat solution, at 50° C. | 11.1 (28) | 18.5 (43) | 22.1 (52) | 11.9 (31) |
|  |  | Elongation (%) after 20-hour immersion Rate of increase (%) in parentheses | Water, at 50° C. | 544 (108) | 521 (105) | 511 (102) | 492 (104) |
|  |  |  | Artificial sweat solution, at 23° C. | 664 (132) | 643 (129) | 615 (123) | 627 (133) |
|  |  |  | Artificial sweat solution, at 50° C. | 892 (177) | 685 (138) | 694 (139) | 585 (124) |
|  |  | Organic solvent impermeability[Note 1] |  | ○ | ◉ | ◉ | ◉ |
| [Note 2]Metal content | Ca (% by weight) | before immersion |  | 1.2 | 1.08 | 1.17 | 1.16 |
|  |  | Water, at 50° C. |  | 1.04 | 0.95 | 1.02 | — |
|  |  | Artificial sweat solution, at 23° C. |  | 1.09 | 0.81 | 0.87 | — |
|  |  | Artificial sweat solution, at 50° C. |  | 0.91 | 0.7 | 0.83 | — |
|  | Zn (% by weight) | before immersion |  | 0.33 | 0.37 | 0.32 | 0.34 |
|  |  | Water, at 50° C. |  | 0.36 | 0.42 | 0.39 | — |
|  |  | Artificial sweat solution, at 23° C. |  | 0.36 | 0.35 | 0.36 | — |
|  |  | Artificial sweat solution, at 50° C. |  | 0.25 | 0.2 | 0.24 | — |
|  | Al (% by weight) | before immersion |  | — | 0.2 | 0.23 | 0.25 |
|  |  | Water, at 50° C. |  | — | 0.2 | 0.24 | — |
|  |  | Artificial sweat solution, at 23° C. |  | — | 0.19 | 0.24 | — |
|  |  | Artificial sweat solution, at 50° C. |  | — | 0.19 | 0.23 | — |

Sample: a film formed on a ceramic plate (thickness: 70 μm), Gelling conditions: at 23° C. for 1 minute, no humectant
[Note 1]Organic solvent impermeability: particularly good = ◉, good = ○, poor = X
[Note 2]Metal content "—" indicating no measurement

(11) Confirmation of Effects of Using Polycarbodiimide in Combination with Zinc Oxide and/or Aluminum Complex Table 11 shows the results of further examining, in response to the results of Examples 6 to 9, 14 and 15 shown in Table 5 and for practical application, the amounts of a polycarbodiimide, zinc oxide and/or an aluminum complex to be added as well as the types of the aluminum complex.

In Examples 35 to 38, while the amount of the polycarbodiimide (E-03A) and that of zinc oxide in the respective aluminum complex, since the citrate complex, the malate complex and the hydroxide complex were all usable, it is seen that a variety of aluminum complexes can be used. In Examples 41 to 43 where the polycarbodiimide (E-03A) was added to the respective dipping compositions in an amount of 1% by weight and the amount of the citrate complex was adjusted, sufficient physical properties were also attained as in other Examples.

TABLE 11

Effects of Using Polycarbodiimide in Combination with Zinc Oxide and/or Aluminum Complex

|  |  |  | Example 35 | Example 36 | Example 37 | Example 38 | Example 39 |
|---|---|---|---|---|---|---|---|
| XNBR |  | Type | NL120H | NL120H | NL120H | NL120H | NL120H |
|  |  | Mooney viscosity ($ML_{(1+4)}$ 100° C.) | 111 | 111 | 111 | 111 | 111 |
|  |  | MEK-insoluble content (% by weight) | 5.6 | 5.6 | 5.6 | 5.6 | 5.6 |
|  |  | Amount of MMA (COOH) (% by weight) | 5.3 | 5.3 | 5.3 | 5.3 | 5.3 |
|  |  | Amount of AN (% by weight) | 28 | 28 | 28 | 28 | 28 |
|  |  | Butadiene (% by weight) | 66.7 | 66.7 | 66.7 | 66.7 | 66.7 |
| (Note 1)Crosslinking agent |  | $Ca^{2+}$ (coagulant) (○: present, X: absent) | ○ | ○ | ○ | ○ | ○ |
|  | Polycarbodiimide | Type | E-03A | E-03A | E-03A | E-03A | E-03A |
|  |  | Added amount (% by weight) | 0.5 | 0.5 | 0.5 | 0.5 | 0.5 |
|  |  | Amount of added ZnO (% by weight) | 0.5 | 0.5 | 0.5 | 0.5 | 0.5 |
|  | Al complex | Type | — | citrate complex | citrate complex | citrate complex | malate complex |
|  |  | Added amount (% by weight) | 0 | 0.1 | 0.3 | 0.5 | 0.5 |
| pH |  | Adjusted value | 10.5 | 10.5 | 10.5 | 10.5 | 10.5 |
|  |  | Modifier | $NH_3$ | $NH_3$ | $NH_3$ | $NH_3$ | $NH_3$ |
| Physical properties |  | Tensile strength (MPa) (target value ≥ 20 MPa) | 45.7 | 41.2 | 41.5 | 47.6 | 48.3 |
|  |  | Fatigue durability (min) (target value ≥ 200 min) | 415 | 464 | 550 | 581 | 835 |
|  |  | Elongation (%) | 516 | 582 | 581 | 510 | 512 |
|  |  | Inhibition of reduction in tensile strength in artificial sweat solution | ○ | ◎ | ◎ | ◎ | ◎ |
|  |  | Organic solvent impermeability | ○ | ◎ | ◎ | ◎ | ◎ |
|  | Metal content(Note 3) | Ca (% by weight) | 1.2 | — | — | 1.08 | 1.17 |
|  |  | Zn (% by weight) | 0.33 | — | — | 0.37 | 0.32 |
|  |  | Al (% by weight) | — | — | — | 0.2 | 0.23 |

|  |  |  | Example 40 | Example 41 | Example 42 | Example 43 |
|---|---|---|---|---|---|---|
| XNBR |  | Type | NL120H | NL120H | NL120H | NL120H |
|  |  | Mooney viscosity ($ML_{(1+4)}$ 100° C.) | 111 | 111 | 111 | 111 |
|  |  | MEK-insoluble content (% by weight) | 5.6 | 5.6 | 5.6 | 5.6 |
|  |  | Amount of MMA (COOH) (% by weight) | 5.3 | 5.3 | 5.3 | 5.3 |
|  |  | Amount of AN (% by weight) | 28 | 28 | 28 | 28 |
|  |  | Butadiene (% by weight) | 66.7 | 66.7 | 66.7 | 66.7 |
| (Note 1)Crosslinking agent |  | $Ca^{2+}$ (coagulant) (○: present, X: absent) | ○ | ○ | ○ | ○ |
|  | Polycarbodiimide | Type | E-03A | E-03A | E-03A | E-03A |
|  |  | Added amount (% by weight) | 0.5 | 1 | 1 | 1 |
|  |  | Amount of added ZnO (% by weight) | 0.5 | 0.5 | 0.5 | 0.5 |
|  | Al complex | Type | hydroxide complex | — | citrate complex | citrate complex |
|  |  | Added amount (% by weight) | 0.5 | 0 | 0.1 | 0.3 |
| pH |  | Adjusted value | 10.5 | 10.5 | 10.5 | 10.5 |
|  |  | Modifier | $NH_3$ | $NH_3$ | $NH_3$ | $NH_3$ |
| Physical properties |  | Tensile strength (MPa) (target value ≥ 20 MPa) | 41.8 | 41.7 | 41.7 | 41.9 |
|  |  | Fatigue durability (min) (target value ≥ 200 min) | 675 | 657 | 741 | 1,026 |
|  |  | Elongation (%) | 481 | 573 | 577 | 568 |
|  |  | Inhibition of reduction in tensile strength in artificial sweat solution | ◎ | ○ | ◎ | ◎ |
|  |  | Organic solvent impermeability | ◎ | ○ | ◎ | ◎ |
|  | Metal content(Note 3) | Ca (% by weight) | 1.16 | — | — | — |
|  |  | Zn (% by weight) | 0.34 | — | — | — |
|  |  | Al (% by weight) | 0.25 | — | — | — |

Sample: a film (thickness: 70 μm) formed on a ceramic plate, Gelling conditions: at 23° C. for 1 minute, no humectant (Note 1)Crosslinking agent The added amount is indicated in % by weight with respect to the solid content of each composition for dip-molded article. For Al complex, the amount is indicated in terms of $Al_2O_3$.

(Note 2)Physical properties: particularly good = "◎", good ="○", poor = "X"

(Note 3)Metal content "—" indicates that the subject metal was not measured.

(12) Confirmation of Physical Properties at Reduced Film Thickness

Examples 44 and 45 shown in Table 12 were conducted to examine if sufficient glove performance would be exerted when the glove thickness was reduced from the conventional glove thickness of 70 μm. Using the dipping compositions having the respective formulations shown in Table 12, gloves were each produced in the same manner as in Comparative Example 1 in accordance with the procedures described in FIGS. 6-1 and 6-2.

In this process, assuming mass production, 2 parts by weight of glycerol was added as a humectant to each dipping composition.

Conventionally, medium-size gloves equivalent to 3.7 g have a thickness of about 70 μm; however, in these Examples, it was aimed at producing a glove of 3.0 to 3.2 g (thickness: 50 to 60 μm).

As a result, it was confirmed that sufficient physical properties were attained not only at the thickness of Example 45 but also at such a small thickness of Example 44.

TABLE 12

Physical Properties at Reduced Cured Film Thickness

| | | Example 44 | Example 45 |
|---|---|---|---|
| XNBR | Type | NL128 | NL128 |
| | Mooney viscosity ($ML_{(1+4)}100°$ C.) | 99 | 99 |
| | MEK-insoluble content (% by weight) | 1.8 | 1.8 |
| | Amount of MMA (COOH) (% by weight) | 5.2 | 5.2 |
| | Amount of AN (% by weight) | 32 | 32 |
| | Butadiene (% by weight) | 62.8 | 62.8 |
| Crosslinking agent | $Ca^{2+}$ (coagulant) (○: present, X: absent) | ○ | ○ |
| | Polycarbodiimide Type | V-02-L2 | V-02-L2 |
| | Added amount (% by weight) | 0.5 | 0.5 |
| | Amount of added ZnO (% by weight) | 0.5 | 1 |
| | Amount of added Al complex (% by weight) | 0 | 0 |
| pH | Adjusted value | 10.5 | 10.5 |
| | Modifier | $NH_3$ | $NH_3$ |
| Physical properties | Film thickness (μm) | 57 | 67 |
| | Tensile strength (MPa) (target value ≥20 MPa) | 36 | 39 |
| | Fatigue durability (min) (target value ≥200 min) | 462 | 698 |
| | Inhibition of reduction in tensile strength in artificial sweat solution | ○ | ○ |
| | Organic solvent impermeability | ○ | ○ |

Sample: Gelling conditions = at 23° C. for 1 minute, Humectant 2% by weight of glycerol
Physical properties: particularly good = "⊚", good = "○", poor = "X"

(13) Confirmation of Temperature Range (Low Temperature) of Curing Step in Glove Production Table 13 shows Examples where the curing temperature was examined for gloves having crosslinks formed by a polycarbodiimide, Zn crosslinks and Ca crosslinks.

Dipping compositions having the respective formulations shown in Table 13 were prepared, and gloves were produced in accordance with the procedures described in FIGS. 6-1 and 6-2. It is noted here, however, that curing was performed under the conditions shown in Table 13.

In the above-described Examples, curing was performed at a temperature of about 120° C. This followed the fact that, in conventional XNBR glove production, it is a general technical knowledge that the temperature of the curing step is 100 to 140° C.

In Examples 46 to 49, as a result of setting the curing temperature at normal temperature (Comparative Example 8) or at 70 to 100° C. (Example 46 to 49), it was found that a glove having sufficient performance can be produced as long as the curing temperature is 70° C. or higher.

In these Examples, taking into consideration the mass-production conditions for carrying out the present invention, such rigorous gelling conditions of 55° C. for 130 seconds that are similar to the actual production conditions were adopted, and a humectant was also added to the respective dipping compositions to produce and examine the thin films of 55 μm in thickness.

TABLE 13

Range of Curing Temperature

| | | | Example 46 | Example 47 | Example 48 | Example 49 | Comparative Example 8 |
|---|---|---|---|---|---|---|---|
| XNBR | Type | | NL120H | NL120H | NL120H | NL120H | NL120H |
| | Mooney viscosity ($ML_{(1+4)}$ 100° C.) | | 111 | 111 | 111 | 111 | 111 |
| | MEK-insoluble content (% by weight) | | 5.6 | 5.6 | 5.6 | 5.6 | 5.6 |
| | Amount of MMA (COOH) (% by weight) | | 5.3 | 5.3 | 5.3 | 5.3 | 5.3 |
| | Amount of AN (% by weight) | | 28 | 28 | 28 | 28 | 28 |
| | Butadiene (% by weight) | | 66.7 | 66.7 | 66.7 | 66.7 | 66.7 |
| Crosslinking agent | $Ca^{2+}$ (coagulant) (○: present, X: absent) | | ○ | ○ | ○ | ○ | ○ |
| | Polycarbodiimide | Type | V-02-L2 | V-02-L2 | V-02-L2 | V-02-L2 | V-02-L2 |
| | | Added amount (% by weight) | 0.5 | 0.5 | 0.5 | 0.5 | 0.5 |
| | Amount of added ZnO (% by weight) | | 1 | 1 | 1 | 1 | 1 |
| | Amount of added Al complex (% by weight) | | 0 | 0 | 0 | 0 | 0 |
| pH | Adjusted value | | 10.5 | 10.5 | 10.5 | 10.5 | 10.5 |
| | Modifier | | $NH_3$ | $NH_3$ | $NH_3$ | $NH_3$ | $NH_3$ |
| Curing conditions | Temperature | | 70° C. | 80° C. | 90° C. | 100° C. | 25° C. |
| | Time | | 10 min | 10 min | 10 min | 10 min | 1 week |
| Physical properties | Tensile strength (MPa) (Target value ≥ 20 MPa) | | 30 | 30 | 30 | 33 | 33 |
| | Fatigue durability (min) (Target value ≥ 200 min) | | 279 | 229 | 336 | 303 | 132 |
| | Inhibition of reduction in tensile strength in artificial sweat solution | | ○ | ○ | ○ | ○ | ○ |
| | Organic solvent impermeability | | ○ | ○ | ○ | ○ | ○ |

Sample: a glove (thickness: 55 μm), Gelling conditions: at 55° C. for 130 seconds, Humectant 2 parts by weight of glycerol
Physical Properties: particularly good = ⊚, good = ○, poor = X

The invention claimed is:

1. A glove dipping composition comprising, at least:
   an elastomer that is constituted by a (meth)acrylonitrile-derived structural unit, an unsaturated carboxylic acid-derived structural unit, and a butadiene-derived structural unit in a polymer main chain;
   a polycarbodiimide;
   zinc oxide and/or an aluminum complex;
   water; and
   at least one pH modifier selected from an ammonium compound and an amine compound, wherein
   said elastomer contains said acrylonitrile or methacrylonitrile-derived structural unit in an amount of 20% by weight to 40% by weight, said unsaturated carboxylic acid-derived structural unit in an amount of 1% by weight to 10% by weight, and said butadiene-derived structural unit in an amount of 50% by weight to 75% by weight,
   said polycarbodiimide comprises at least one polycarbodiimide containing a hydrophilic segment in its molecular structure,
   said polycarbodiimide has an average polymerization degree of 3.8 or higher and a carbodiimide equivalent of 260 to 440 and is added in an amount of 0.3% by weight to 2.0% by weight with respect to the total solid content of said glove dipping composition,
   zinc oxide and/or said aluminum complex is added in an amount of 0.1% by weight to 5.6% by weight with respect to the total solid content of said glove dipping composition, and
   said glove dipping composition has a pH of 9.0 to 11.5.

2. The glove dipping composition according to claim 1, wherein said dipping composition contains zinc oxide, and the amount thereof is 0.1% by weight to 4.0% by weight with respect to the total solid content of said glove dipping composition.

3. The glove dipping composition according to claim 1, wherein said dipping composition contains zinc oxide and said aluminum complex, and the total amount thereof is 0.1% by weight to 5.6% by weight with respect to the total solid content of said glove dipping composition.

4. The glove dipping composition according to claim 1, further comprising a humectant.

5. A method of producing a glove, said method comprising:
   (1) a step of immersing a glove forming mold in a liquid coagulant containing calcium ions so as to allow said coagulant to adhere to said glove forming mold;
   (2) a step of leaving the glove dipping composition according to claim 1 to stand with stirring;
   (3) a dipping step of immersing said glove forming mold, to which said coagulant has thus adhered in said step (1), in said glove emulsion composition;
   (4) a gelling step of leaving said glove forming mold, to which said glove dipping composition has thus adhered, to stand at a temperature for a period that satisfy the following conditions: a temperature and a period that allow said calcium ions contained in said coagulant to infiltrate into said elastomer contained in said glove dipping composition and to thereby induce gelation, without causing ammonium salts or amine salts of said elastomer contained in said glove dipping composition to be converted back to carboxyl groups and without causing said hydrophilic segment of said polycarbodiimide to be opened;
   (5) a leaching step of removing impurities from a cured film precursor thus formed on said glove forming mold;
   (6) a beading step of, after said leaching step, winding the cuff portion of the resulting glove;
   (7) a precuring step of heating and drying said cured film precursor that has been subjected to said beading step; and
   (8) a curing step of heating said cured film precursor to obtain a cured film, said heating being performed at a temperature for a period that are sufficient for said ammonium salts or amine salts of said elastomer to be converted back to carboxyl groups, said carbodiimide groups of said polycarbodiimide to be exposed, and said carboxyl groups of said elastomer to react with said carbodiimide groups,
   which steps (3) to (8) are performed in the order mentioned.

6. The method of producing a glove according to claim 5, wherein said glove dipping composition in said step (2) contains a humectant, and said conditions of said gelling step of (4) are: at 50° C. to 70° C. for 20 seconds to less than 20 minutes.

7. The method of producing a glove according to claim 5, wherein said glove dipping composition in said step (2) contains no humectant, and
   said conditions of said gelling step of (4) are: at 15° C. to 25° C. for 20 seconds to 20 minutes, or at 50° C. to 70° C. for 20 seconds to 3 minutes.

8. The method of producing a glove according to claim 5, wherein said gelling step of (4) is performed under a condition of 40% RH to 60% RH.

9. A glove produced by the method according to claim 5, wherein said glove has the following performances:
   (1) a fatigue durability of 200 minutes or longer; and
   (2) a tensile strength of 20 MPa or higher.

10. A glove dipping composition comprising, at least:
    an elastomer that contains a (meth)acrylonitrile-derived structural unit, an unsaturated carboxylic acid-derived structural unit, and a butadiene-derived structural unit in a polymer main chain;
    a polycarbodiimide;
    zinc oxide and an aluminum complex;
    water; and
    at least one pH modifier selected from an ammonium compound and an amine compound, wherein
    said elastomer contains said acrylonitrile or methacrylonitrile-derived structural unit in an amount of 20% by weight to 40% by weight, said unsaturated carboxylic acid-derived structural unit in an amount of 1% by weight to 10% by weight, and said butadiene-derived structural unit in an amount of 50% by weight to 75% by weight,
    said polycarbodiimide comprises at least one polycarbodiimide containing a hydrophilic segment in its molecular structure,
    said polycarbodiimide has an average polymerization degree of 3.8 or higher and a carbodiimide equivalent of 260 to 600 and is added in an amount of 0.1% by weight to 4.0% by weight with respect to the total solid content of said glove dipping composition,
    zinc oxide and said aluminum complex is added in an amount of 0.1% by weight to 5.6% by weight with respect to the total solid content of said glove dipping composition, and
    said glove dipping composition has a pH of 9.0 to 11.5.

11. The glove dipping composition according to claim 10, further comprising a humectant.

12. A method of producing a glove, said method comprising:
(1) a step of immersing a glove forming mold in a liquid coagulant containing calcium ions so as to allow said coagulant to adhere to said glove forming mold;
(2) a step of leaving the glove dipping composition according to claim 10 to stand with stirring;
(3) a dipping step of immersing said glove forming mold, to which said coagulant has thus adhered in said step (1), in said glove emulsion composition;
(4) a gelling step of leaving said glove forming mold, to which said glove dipping composition has thus adhered, to stand at a temperature for a period that satisfy the following conditions: a temperature and a period that allow said calcium ions contained in said coagulant to infiltrate into said elastomer contained in said glove dipping composition and to thereby induce gelation, without causing ammonium salts or amine salts of said elastomer contained in said glove dipping composition to be converted back to carboxyl groups and without causing said hydrophilic segment of said polycarbodiimide to be opened;
(5) a leaching step of removing impurities from a cured film precursor thus formed on said glove forming mold;
(6) a beading step of, after said leaching step, winding the cuff portion of the resulting glove;
(7) a precuring step of heating and drying said cured film precursor that has been subjected to said beading step; and
(8) a curing step of heating said cured film precursor to obtain a cured film, said heating being performed at a temperature for a period that are sufficient for said ammonium salts or amine salts of said elastomer to be converted back to carboxyl groups, said carbodiimide groups of said polycarbodiimide to be exposed, and said carboxyl groups of said elastomer to react with said carbodiimide groups,
which steps (3) to (8) are performed in the order mentioned.

13. The method of producing a glove according to claim 12, wherein said glove dipping composition in said step (2) contains a humectant, and said conditions of said gelling step of (4) are: at 50° C. to 70° C. for 20 seconds to less than 20 minutes.

14. The method of producing a glove according to claim 12, wherein said glove dipping composition in said step (2) contains no humectant, and said conditions of said gelling step of (4) are: at 15° C. to 25° C. for 20 seconds to 20 minutes, or at 50° C. to 70° C. for 20 seconds to 3 minutes.

15. The method of producing a glove according to claim 12, wherein said gelling step of (4) is performed under a condition of 40% RH to 60% RH.

16. A glove produced by the method according to claim 12, wherein said glove has the following performances:
(1) a fatigue durability of 200 minutes or longer; and
(2) a tensile strength of 20 MPa or higher.

* * * * *